US008691829B2

(12) United States Patent
Ulrich

(10) Patent No.: US 8,691,829 B2
(45) Date of Patent: Apr. 8, 2014

(54) TREATMENT OF LIVER DISORDERS WITH PI3K INHIBITORS

(75) Inventor: Roger G. Ulrich, Foster City, CA (US)

(73) Assignee: Gilead Calistoga LLC, Foster City, CA (US)

( * ) Notice: Subject to any disclaimer, the term of this patent is extended or adjusted under 35 U.S.C. 154(b) by 116 days.

(21) Appl. No.: 13/386,387

(22) PCT Filed: Jul. 21, 2010

(86) PCT No.: PCT/US2010/042801
§ 371 (c)(1),
(2), (4) Date: Mar. 27, 2012

(87) PCT Pub. No.: WO2011/011550
PCT Pub. Date: Jan. 27, 2011

(65) Prior Publication Data
US 2012/0178767 A1 Jul. 12, 2012

Related U.S. Application Data

(60) Provisional application No. 61/227,343, filed on Jul. 21, 2009.

(51) Int. Cl.
A61K 31/52 (2006.01)
A61P 35/00 (2006.01)

(52) U.S. Cl.
USPC .................................. 514/260.1; 514/263.21

(58) Field of Classification Search
USPC .......................................... 514/260.1, 263.21
See application file for complete search history.

(56) References Cited

U.S. PATENT DOCUMENTS

| | | | |
|---|---|---|---|
| 3,322,756 A | 5/1967 | Ruschig et al. | |
| 3,691,016 A | 9/1972 | Patel | |
| 3,897,432 A | 7/1975 | Shen et al. | |
| 3,969,287 A | 7/1976 | Jaworek et al. | |
| 3,984,555 A | 10/1976 | Amschler et al. | |
| 4,179,337 A | 12/1979 | Davis et al. | |
| 4,183,931 A | 1/1980 | Wolfe et al. | |
| 4,195,128 A | 3/1980 | Hildebrand et al. | |
| 4,225,489 A | 9/1980 | Rolf et al. | |
| 4,229,537 A | 10/1980 | Hodgins et al. | |
| 4,247,642 A | 1/1981 | Hirohara et al. | |
| 4,289,872 A | 9/1981 | Denkewalter et al. | |
| 4,301,144 A | 11/1981 | Iwashita et al. | |
| 4,330,440 A | 5/1982 | Ayers et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,925,673 A | 5/1990 | Steiner et al. | |
| 5,013,556 A | 5/1991 | Woodle et al. | |
| 5,225,347 A | 7/1993 | Goldberg et al. | |
| 5,229,490 A | 7/1993 | Tam | |
| 5,378,725 A | 1/1995 | Bonjouklian et al. | |
| 5,480,906 A | 1/1996 | Creemer et al. | |
| RE35,862 E | 7/1998 | Steiner et al. | |
| 5,858,753 A | 1/1999 | Chantry et al. | |
| 5,882,910 A | 3/1999 | Chantry et al. | |
| 5,948,664 A | 9/1999 | Williams et al. | |
| 5,985,589 A | 11/1999 | Chantry et al. | |
| 6,046,049 A | 4/2000 | Monia et al. | |
| 6,048,970 A | 4/2000 | Lal et al. | |
| 6,277,981 B1 | 8/2001 | Tu et al. | |
| 6,291,220 B1 | 9/2001 | Williams et al. | |
| 6,369,038 B1 | 4/2002 | Blumenfeld et al. | |
| 6,410,224 B1 | 6/2002 | Stinchcomb et al. | |
| 6,426,337 B1 | 7/2002 | Cox et al. | |
| 6,482,623 B1 | 11/2002 | Vanhaesebroeck et al. | |
| 6,518,277 B1 | 2/2003 | Sadhu et al. | |
| 6,667,300 B2 | 12/2003 | Sadhu et al. | |
| 6,696,250 B1 | 2/2004 | Cech et al. | |
| 6,800,620 B2 | 10/2004 | Sadhu et al. | |
| 6,949,535 B2 | 9/2005 | Sadhu et al. | |
| 7,932,260 B2 | 4/2011 | Fowler et al. | |
| 8,138,195 B2 | 3/2012 | Sadhu et al. | |
| 8,207,153 B2 | 6/2012 | Fowler et al. | |
| 2004/0023390 A1 | 2/2004 | Davidson et al. | |
| 2004/0092561 A1 | 5/2004 | Ruckle et al. | |
| 2004/0121996 A1 | 6/2004 | Barvian et al. | |
| 2004/0138199 A1 | 7/2004 | Gogliotti et al. | |
| 2004/0242631 A1 | 12/2004 | Garlich et al. | |
| 2004/0248953 A1 | 12/2004 | Gogliotti et al. | |
| 2004/0248954 A1 | 12/2004 | Gogliotti et al. | |
| 2004/0259926 A1 | 12/2004 | Bruendl et al. | |
| 2005/0004195 A1 | 1/2005 | Para et al. | |
| 2005/0020630 A1 | 1/2005 | Connolly et al. | |
| 2005/0020631 A1 | 1/2005 | Gogliotti et al. | |
| 2005/0043239 A1 | 2/2005 | Douangpanya et al. | |
| 2005/0054614 A1 | 3/2005 | Diacovo et al. | |
| 2005/0239809 A1 | 10/2005 | Watts et al. | |
| 2005/0261317 A1 | 11/2005 | Sadhu et al. | |
| 2006/0079538 A1 | 4/2006 | Hallahan et al. | |
| 2006/0106038 A1 | 5/2006 | Bouscary et al. | |

(Continued)

FOREIGN PATENT DOCUMENTS

EP 0 364 598 A1 4/1990
EP 0 525 960 A1 2/1993

(Continued)

OTHER PUBLICATIONS

"Acute Congestive Heart Failure", Thomas N. Levin, Postgraduate Medicine, vol. 101, No. 1, 1997.

(Continued)

Primary Examiner — Raymond Henley, III
(74) Attorney, Agent, or Firm — Morrison & Foerster LLP

(57) ABSTRACT

The invention provides methods to treat certain liver disorders by administering a compound that inhibits PD K isoforms, particularly the delta isoform. It further provides specific compounds useful for these methods and ways to identify subjects who are particularly suitable for receiving these treatments.

22 Claims, 1 Drawing Sheet

(56) References Cited

U.S. PATENT DOCUMENTS

| | | |
|---|---|---|
| 2008/0275067 A1 | 11/2008 | Fowler et al. |
| 2008/0287469 A1 | 11/2008 | Diacovo et al. |
| 2010/0029693 A1 | 2/2010 | Douangpanya et al. |
| 2010/0152211 A1 | 6/2010 | Sadhu et al. |
| 2010/0168139 A1 | 7/2010 | Sadhu et al. |
| 2010/0202963 A1 | 8/2010 | Gallatin et al. |
| 2010/0249155 A1* | 9/2010 | Evarts et al. ............ 514/263.21 |
| 2010/0256167 A1 | 10/2010 | Fowler et al. |
| 2010/0256168 A1 | 10/2010 | Fowler et al. |
| 2011/0044942 A1 | 2/2011 | Puri et al. |
| 2011/0230465 A1 | 9/2011 | Stammers et al. |
| 2012/0015964 A1 | 1/2012 | Fowler et al. |
| 2012/0040980 A1 | 2/2012 | Huggins et al. |
| 2012/0135994 A1 | 5/2012 | Sadhu et al. |
| 2012/0172591 A1 | 7/2012 | Sadhu et al. |
| 2012/0178767 A1* | 7/2012 | Ulrich ........................ 514/260.1 |
| 2013/0116266 A1 | 5/2013 | Fowler et al. |
| 2013/0231356 A1 | 9/2013 | Kesicki et al. |

FOREIGN PATENT DOCUMENTS

| | | |
|---|---|---|
| EP | 0 525 960 B1 | 2/1993 |
| EP | 0 675 124 A2 | 10/1995 |
| EP | 0 675 124 A3 | 10/1995 |
| EP | 0 716 857 A1 | 6/1996 |
| EP | 0 716 857 B1 | 6/1996 |
| EP | 0 884 310 A1 | 12/1998 |
| EP | 0 884 310 B1 | 12/1998 |
| EP | 0 900 568 A2 | 3/1999 |
| EP | 0 900 568 A3 | 3/1999 |
| EP | 1 939 203 A2 | 7/2008 |
| EP | 1 939 203 A3 | 7/2008 |
| GB | 1 356 763 A | 6/1974 |
| GB | 2 017 097 A | 10/1979 |
| JP | 55 118917 A2 | 9/1980 |
| JP | 55 118918 A2 | 1/1981 |
| JP | 56 002322 A2 | 1/1981 |
| WO | WO-93/21259 A1 | 10/1993 |
| WO | WO-94/17090 A1 | 8/1994 |
| WO | WO-95/24379 A1 | 9/1995 |
| WO | WO-96/04923 A1 | 2/1996 |
| WO | WO-96/25488 A1 | 8/1996 |
| WO | WO-96/32478 A1 | 10/1996 |
| WO | WO-97/34631 A1 | 9/1997 |
| WO | WO-97/41097 A2 | 11/1997 |
| WO | WO-97/43276 A1 | 11/1997 |
| WO | WO-97/46688 A1 | 12/1997 |
| WO | WO-98/33802 A1 | 8/1998 |
| WO | WO-98/38173 A1 | 9/1998 |
| WO | WO-99/08501 A2 | 2/1999 |
| WO | WO-99/08501 A3 | 2/1999 |
| WO | WO-99/34804 A1 | 7/1999 |
| WO | WO-01/00881 A1 | 1/2001 |
| WO | WO-01/30768 A1 | 5/2001 |
| WO | WO-01/30768 C2 | 5/2001 |
| WO | WO-01/53266 A1 | 7/2001 |
| WO | WO-01/57034 A1 | 8/2001 |
| WO | WO-01/81346 A2 | 11/2001 |
| WO | WO-01/81346 A3 | 11/2001 |
| WO | WO-03/035075 A1 | 5/2003 |
| WO | WO-03/106622 A2 | 12/2003 |
| WO | WO-03/106622 A3 | 12/2003 |
| WO | WO-2004/007491 A1 | 1/2004 |
| WO | WO-2004/012768 A1 | 2/2004 |
| WO | WO-2004/026285 A2 | 4/2004 |
| WO | WO-2004/026285 A3 | 4/2004 |
| WO | WO-2004/029055 A1 | 4/2004 |
| WO | WO-2004/052373 A1 | 6/2004 |
| WO | WO-2004/056820 A1 | 7/2004 |
| WO | WO-2004/089925 A1 | 10/2004 |
| WO | WO-2004/108708 A1 | 12/2004 |
| WO | WO-2004/108709 A1 | 12/2004 |
| WO | WO-2004/108713 A1 | 12/2004 |
| WO | WO-2004/108713 C1 | 12/2004 |
| WO | WO-2004/108715 A1 | 12/2004 |
| WO | WO-2004/108715 C1 | 12/2004 |
| WO | WO-2005/016348 A1 | 2/2005 |
| WO | WO-2005/016349 A1 | 2/2005 |
| WO | WO-2005/067901 A2 | 7/2005 |
| WO | WO-2005/067901 A3 | 7/2005 |
| WO | WO-2005/112935 A1 | 12/2005 |
| WO | WO-2005/113556 A1 | 12/2005 |
| WO | WO-2005/120511 A1 | 12/2005 |
| WO | WO-2007/076085 A2 | 7/2007 |
| WO | WO-2008/064018 A1 | 5/2008 |
| WO | WO-2009/046448 A1 | 4/2009 |
| WO | WO-2009/058361 A1 | 5/2009 |
| WO | WO-2009/088990 A1 | 7/2009 |
| WO | WO-2010/057048 A1 | 5/2010 |
| WO | WO-2010/065923 A2 | 6/2010 |
| WO | WO-2010/065923 A3 | 6/2010 |
| WO | WO-2010/123931 A1 | 10/2010 |

OTHER PUBLICATIONS

Sutton, A. (Jun. 9, 2006). "Baylor, St. Luke's study uses gene therapy as pancreatic cancer", located at <http://www.bcm.edu/news/item.cfm?newsID=640>, last visited on Sep. 2, 2006, 2 pages.

Anonymous (2006). "Cardiovascular Disease: Treatment for Stroke", Stanford Hospital & Clinics, located at <http://www.slanfordhospital.com/healthLib/atoz/cardiac/stktreat.html>, last visited on Sep. 19, 2006, 2 pages.

Marchione et al. (2006). "Drugs hold promise in kidney cancer fight", located at <http://www.ledger-enquirer.com/mld/ledgerenquirer/living/health/14744763.htm>, last visited on Sep. 2, 2006, 3 pages.

Anonymous (2006). "Heart Disease", WebMD, located at <http://www.webmd.com/contont/pages/9/1675_57842.htm>, as retrieved on Sep. 14, 2006, 1 page.

Anonymous, (2010). "Multiple Sclerosis", located at <hitp://www.health.nytimes.com/health/guides/disease/multiple-sclerosis/overview.html>, last visited Aug. 1, 2010, 4 pages.

Anonymous, (2004). "NIH Heart Disease & Stroke Research: Fact Sheet", American Heart Association, located at <http://www.americanheart.org/presenter.jhtml?identifier=3010188>, last visited Feb. 17, 2004, 1 page.

Anonymous (2010). "Spinal Cord Injury", located at <http://www.medicinecabinet.com/spinal_cord_injury/page.htm>, last visited on Aug. 1, 2010, 3 pages.

Anonymous (2010) "Systemic Lupus Erythematosus", located at <http://www.nlm.nih.gov/medlineplus/ency/article/000435.htm>, last visited Aug. 1, 2010, 4 pages.

"Chemia Lekow", ed. E. Pawelczyk, PZWL, Warszawa 1986, see, part 1.2.2.

"Preparatyka Organiczna", ed. A.I. Vogel, WNT, Warszawa 1984, page, e.g. 83.

Abu-Duhier et al., Br. J. Haematol. (2001) 113:983-988.

Adamkiewicz, "Tumor Angiogenesis: Mechanisms" IMT—Marburg—Research Group, retrieved from the internet on Apr. 13, 2004, located at: <http://www.imt.uni-marburg.de/~adamkiew/mechanism.html>, 2 pages.

Advisory Action from U.S. Appl. No. 11/596,092, mailed on Jul. 27, 2010.

Ager et al., J. Med. Chem. (1977) 20:379-386.

Ali et al., Nature (2004) 431:1007-1011.

Alon et al., "The molecular basis of leukocyte adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, located at <http://www weizmann.ac.il/Biology/open_day_2002/book/open_alon.pdf>, 2 pages.

Amendment from U.S. Appl. No. 09/841,341, filed Aug. 21, 2002.

Amendment from U.S. Appl. No. 10/027,591, filed Jun. 3, 2003.

Amendment in Response to Final Office Action from U.S. Appl. No. 11/596,092, filed Jul. 19, 2010.

Amendment in Response to Non-Final Office Action/Restriction Requirement from U.S. Appl. No. 11/884,566, filed Jun. 7, 2010.

Amendment in Response to Non-Final Office Action from U.S. Appl. No. 10/918,803, filed Oct. 1, 2008.

(56) References Cited

OTHER PUBLICATIONS

Amendment in Response to Non-Final Office Action from U.S. Appl. No. 10/918,803, filed Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Sep. 4, 2009.
Amendment in Response to Non-Final Office Action from U.S. Appl. No. 11/110,204, filed Jun. 4, 2010.
Amendment in Response to Non-Final Office Action from U.S. Appl. No. 11/596,092, filed Nov. 10, 2009.
Amendment in Response to Non-Final Office Action from U.S. Appl. No. 11/596,092, filed Mar. 24, 2010.
Amendment Under 37 C.F.R. § 1.111 from U.S. Appl. No. 11/129,006, filed Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed Sep. 1, 2010.
Amin et al., Circ Res (2003) 93(4):321-329.
Amine, M.S. et al. (Nov. 1998). "Uses of Quinazolin-2-[(β-Propionoyl) Isothiocyanate]-4-One as a Building Block in Synthesis of Some Heterocyclic Compounds of Expected Biological Activity," *Indian Journal of Chemistry* 37B(11):1153-1156.
Angel, Activities of Phosphoinositide Kinase-3 (PI3K) (1999) retrieved from the internet on May 22, 2003, URL: http://www.chem.csustan.edu/chem4400/SJBR/angel99.htm.
Angio World, "How Angiogenesis Complicates Psoriasis" (2001) retrieved from the internet on Apr. 13, 2004, located at <http://www.angioworldcom/psoriasis.htm>,1 page.
Annabi et al., J. Cell. Biochem. (2004) 91:1146-1158.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Bader, A.G. et al. (2005). "Oncogenic PI3K Deregulates Transcription and Translation," *Nature Reviews Cancer* 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," *Az. J. Pharm. Sci.* 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Bergers et al., Science (1999) 284:808-812.
Bharadwaj et al., J. Immunol. (2001) 166:6735-6741.
Binetruy-Tournaire et al., Embo J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.
Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44th Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," Haematologica 95(s2):466, Abstract No. 1130.
Brunn et al., EMBO J. (1996) 15:5256-5267.
Burgering et al., Nature (1995) 376:599-602.
Butcher et al., Science (1996) 272:60-66.
Cadwallader et al., J. Immunol. (2002) 169:3336-3344.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
CAS Abstract, Accession No. DN 86:83505 [1977] pp. 112-118.
Cebon et al., Cancer Immun. (2003) 3:7-25.
Chang et al., Exp. Opin. Ther. Patents (2001) 11:45-59.
Chang, BioMed. Eng. Online (2003) 2:12.
Chantry, D. et al. (1997). "p110δ, a Novel Phosphatidylinositol 3-Kinase Catalytic Subunit That Associates with p85 and Is Expressed Predominantly in Leukocytes," *J. Biol. Chem.* 272(31):19236-19241.
Chen et al., Blood (2000) 96:3181-3187.
Chern et al., Chem. Pharm. Bull. (1998) 46(6):928-933.
Chern et al., Chemical Abstracts (1998) 129(16):676.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.
Cleary, J.M. et al. (2010). "Development of Phosphoinositide-3 Kinase Pathway Inhibitors for Advanced Cancer," *Curr. Oncol. Rep.* 12:87-94.
Coligan et al., Current Protocols in Protein Science (2002) 3:15-20.
Constantin et al., Immunity (2000) 13:759-769.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dania et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351:95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.
Doggett et al., Biophys. J. (2002) 83:194-205.
Domanig, R. (1981). "Chinazolinone, 2. Mitt: Synthese Und Einige Reaktionen Von 2-Azidomethyl-3-Aryl-4-Chinazolinonen," Monatshefte fuer Chemie 112(10):1195-1202. (English translation of abstract only).
Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
El-Fattah et al., Indian J Hetercyclic Chemistry (1995) 4:199-202.
El-Feky, S.A. et al. (1985). "Synthesis of Certain New Sulfur-Containing Quinazolinone Derivatives Likely to Possess CNS Depressant Action," *Egyptian Journal of Pharmaceutical Sciences* 24(1-4):39-47.
El-Feky et al., Chemical Abstracts (1987) 106(13):650.
El-Feky et al., Chemical Abstracts (1999) 131(23):497.
El-Feky, S.A. (Aug. 1998). "Novel Quinazolinones From 2-Cyanomethyl-3-Phenyl-4(3H) Quinazolinone," Bollettino Chimico Farmaceutico 137(7):286-289.
Engelman et al., Nature Reviews (2006) 7:606-619.
Environmental Protection Agency, EPA-Radiation Information (EPA's Radiation Protection Program:Information) "Ionizing Radiation Fact Sheet Series No. 1" (May 1998) Retrieved on Apr. 21, 2004: http://www.epa.gov/radiation/docs/ionize/ionize.htm.
Erbagci et al., Clin. Biochem. (2001) 34:645-650.

(56) References Cited

OTHER PUBLICATIONS

Estey, Cancer (2001) 92:1059-1073.
Etzioni, Pediatr. Res. (1996) 39:191-198.
European Search Report mailed Mar. 29, 2011, for EP Patent Application No. 10163434.3, filed on Apr. 24, 2001, 9 pages.
Faffe et al., Eur. Respir. J. (2000) 15:85-91.
Fantl et al., Ann. Rev. Biochem. (1993) 62:453-481.
Faust et al., Blood (2000) 96:719-726.
Final Office Action from U.S. Appl. No. 10/918,803, mailed on Jan. 8, 2009.
Final Office Action from U.S. Appl. No. 11/129,006, mailed on Oct. 5, 2010.
Final Office Action from U.S. Appl. No. 11/596,092, mailed on May 18, 2010.
Final Office Action mailed on Oct. 24, 2011, for U.S. Appl. No. 12/732,128, filed Mar. 25, 2010, 8 pages.
Final Office Action mailed on Feb. 15, 2012, for U.S. Appl. No. 12/732,124, filed Mar. 25, 2010, 12 pages.
Final Office Action mailed on Jun. 7, 2012, for U.S. Appl. No. 11/129,006, filed May 12, 2005, 14 pages.
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p110δ Isoform of Phosphatidylinositol 3-Kinase (PI3K), in Patients with Select Hematologic Malignancies," Journal of Clinical Oncology 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," *Blood* 114(22):380, Abstract 922.
Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," Haematologica 94(s2):303, Abstract 0744.
Folkman, Curr. Mol. Med. (2003) 3:643-651.
Folkman, Nat. Med. (1995) 1:27-31.
Fraser et al., Science (1991) 251:313-316.
Frey et al., Lancet (2008) 372(9643):1088-1099 (abstract).
Freyssinier et al., Br. J. Haematol. (1999) 106:912-922.
Fruman et al., Ann. Rev. Biochem. (1998) 67:481-507.
Fruman et al., Semin. Immunol. (2002) 14:7-18.
Furman, R.R. (Jul. 2010). "New Agents in Early Clinical Trials for CLL Therapy," Clinical Advances in Hematology & Oncology 8(7):475-476.
Garcia-Barros et al., Science (2003) 300:1155-1159.
Genbank Accession No. AK040867, last updated Sep. 19, 2008, located at <http://www.ncbi.nlm.nih.gov/nuccore/26334014>, last visited on Apr. 16, 2010, 6 pages.
GenBank Accession No. AR255866, last updated Dec. 20, 2002, located at <http://www.ncbi.nlm.nih.gov/nuccore/27305059>, last visited on Apr. 16, 2010, 2 pages.
GenBank Accession No. BC035203, last updated Aug. 11, 2006, located at <http://www.ncbi.nlm.nih.gov/nuccore/23270986>, last visited on Apr. 16, 2010, 5 pages.
GenBank Accession No. NM_005026, last updated Apr. 11, 2010, located at <http://www.ncbi.nlm.nih.gov/nuccore/15654404>, last visited Apr. 16, 2010, 7 pages.
GenBank Accession No. NM_008840, last updated on Mar. 5, 2010, located at <http://www.ncbi.nlm.nih.gov/nuccore/255708435>, last visited on Apr. 16, 2010, 5 pages.
GenBank Accession No. U57843, last updated on May 9, 1997, located at <http://www.ncbi.nlm.nih.gov/nuccore/U57843>, last visited on Aug. 9, 2011, 2 pages.
GenBank Accession No. U86453, last updated on Jul. 7, 1998, located at <http://www.ncbi.nlm.nih.gov/nuccore/2317893>, last visited on Apr. 16, 2010, 3 pages.
GenBank Accession No. U86587, last updated Jul. 7, 1998, located at <http://www.ncbi.nlm.nih.gov/nuccore/2331237>, last visited on Apr. 16, 2010, 3 pages.
GenBank Accession No. XM_345606, last updated Jun. 22, 2006, located at <http://www.ncbi.nlm.nih.gov/nuccore/109475856?report=genbank>, last visited on Apr. 16, 2010, 3 pages.
GenBank Accession No. Y10055, last updated Oct. 7, 2008, located at <http://www.ncbi.nlm.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) 9th ed., pp. 11-16.
Harlan, Haematology 96, the Education Program Book of the 26th Congress of the International Society of Haematology. Singapore, 1996.
Harning et al., Transplantation (1991) 52:842-845.
Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
Hattori, H. et al. (May/Jun. 2010). "Reactive Oxygen Species as Signaling Molecules in Neutrophil Chemotaxis," *Communicative and Integrative Biology* 3(3):278-281.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.
Heit et al., J. Cell Biol. (2002) 159:91-102.
Hellman, Cancer: Principles and Practice of Oncology (1993) 4th ed., vol. 1:248-275.
Herman, S.E.M. et al. (Sep. 23, 2010). "Phosphatidylinositol 3-Kinase-δ Inhibitor CAL-101 Shows Promising Preclinical Activity in Chronic Lymphocytic Leukemia by Antagonizing Intrinsic and Extrinsic Cellular Survival Signals," *Blood* 116(12):2078-2088.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Horgan et al., Am. J. Physiol. (1991) 261:H1578-H1584.
Hsieh, S.N. (2003). "Identification of PI3Kγ in Endothelial Cells and Its Involvement in Sphingosine 1-Phosphate Mediated Endothelial Cell Migration," Dissertation, Friedrick Schiller University, Jena, Germany, 104 pages.
Hu et al., Mol. Cell. Biol. (1993) 13:7677-7688.

(56) References Cited

OTHER PUBLICATIONS

Hu et al., Science (1995) 268:100-102.
Hunter, Cell (1995) 83:1-4.
Hussong et al., Blood (2000) 95:309-313.
Ikeda, H. et al. (Feb. 2009). "CAL-101: A Selective Inhibitor of PI3K p110δ for the Treatment of Multiple Myeloma," *Clinical Lymphoma and Myeloma* 9(Supp. 1):S98-S99.
Ikeda, H. et al. (Nov. 16, 2008). "CAL-101, a Specific Inhibitor of the p110δ Isoform of Phosphatidylinositide 3-Kinase Induces Cytotoxicity in Multiple Myeloma (MM)," *Blood* 112(11):950, Abstract No. 2753.
Ikeda, H. et al. (Sep. 2, 2010). "PI3K/p110δ is a Novel Therapeutic Target in Multiple Myeloma," *Blood* 116(9):1460-1468.
International Preliminary Report on Patentability for PCT/US2006/005621, issued on Aug. 21, 2007, 8 pages.
International Preliminary Report on Patentability mailed on Jan. 24, 2012, for PCT Application No. PCT/US2010/042801, filed on Jul. 21, 2010, 11 pages.
International Search Report for International (PCT) Patent Application Serial No. PCT/US2004/026436, dated Dec. 2, 2004.
International Search Report for International (PCT) Patent Application Serial No. PCT/US2004/029561, dated May 25, 2005.
International Search Report for International (PCT) Patent Application Serial No. PCT/US2004/026834, dated Nov. 29, 2004.
International Search Report for International (PCT) Patent Application Serial No. PCT/US2004/037860, dated May 6, 2005.
International Search Report mailed on Aug. 29, 2005, for PCT Application No. PCT/US2005/016778, filed on May 12, 2005, 4 pages.
International Search Report mailed on Sep. 15, 2006 for PCT Application No. PCT/US2006/005621, filed on Feb. 16, 2006, 4 pages.
International Search Report mailed on Oct. 22, 2010 for PCT Application No. PCT/US2010/042801, filed on Jul. 21, 2010, 8 pages.
Interview Summary from U.S. Appl. No. 10/918,825, mailed on Jun. 14, 2006.
Ismail and Sayed, Indian Journal of Chemistry (1982) 21B(5):461-462.
Ismail et al., Chemical Abstracts (1983) vol. 98, No. 1, p. 406.
Isobe et al., Science (1992) 255:1125-1127.
Johnson et al., Intl. J. Rad. One. Biol. Phys. (1976) 1:659-670.
Johnson et al., J. Endourol. (2003) 17:557-562.
Jordan, Nature Reviews: Drug Discovery (2003) 2:205.
Jou et al., Mol. Cell. Biol. (2002) 22:8580-8591.
Kahl, B.S. (May 2010). "Novel Agents for Non-Hodgkin Lymphoma," *Clinical Advances in Hematology & Oncology* 8(5)(Suppl. 10):10-15.
Kakimoto et al., Cell. Immunol. (1992) 142:326-337.
Kallman et al., Canc. Res. (1972) 32:483-490.
Kandel et al., Exp. Cell Res. (1999) 253:210-229.
Kawasaki et al., J. Immunol. (1993) 150:1074-1083.
Kim et al., Endocrin. (2000) 141:1846-1853.
Kim, Retrieved from the Internet on Apr. 13, 2004: URL: http://www.math.umn.edu/~yjkim/biopaper/timy,html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Lannutti, B.J. et al. (Apr. 2009). "CAL-101, a Specific PI3K p110δ Inhibitor for the Treatment of Hematological Maglignancies," *Proceedings of the American Association for Cancer Research* 50:1400, Abstract No. #SY32-2.
Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," *Blood* 112(11):12, Abstract No. 16.
Lannutti, B.J. et al. (Nov. 20, 2009). "CAL-101, an Oral P110δ Selective Phosphatidylinositol-3-Kinase (PI3K) Inhibitor for the Treatment of B Cell Malignancies Inhibits PI3K Signaling, Cellular Viability and Protective Signals of the Microenvironment," *Blood* 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," *Haematologica* 95(52):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," *Haematologica* 94(52):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172:7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.
Marley et al., Br. J. Haematol. (May 2004) 125:500-511.
May, S.E. et al. (Nov. 16, 2008). "CAL-101, a Selective Inhibitor of the p110δ Isoform of Phosphatidylinositol 3-Kinase, Effectively Induces Apoptosis in Primary Chronic Lumphocytic Leukemia Cells Providing a Novel Therapeutic Strategy for the Treatment of this Disease," *Blood* 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.
Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
Ninomiya et al., J. Biol. Chem. (1994) 269:22732-22737.
Non Final Office Action from U.S. Appl. No. 11/596,092, mailed on Dec. 24, 2009.
Non-Final Office Action from U.S. Appl. No. 09/841,341, mailed on Apr. 25, 2002.
Non-Final Office Action from U.S. Appl. No. 10/027,591, mailed on Feb. 26, 2003.
Non-Final Office Action from U.S. Appl. No. 10/918,803, mailed on Apr. 1, 2008.
Non-Final Office Action from U.S. Appl. No. 10/918,803, mailed on Mar. 16, 2010.
Non-Final Office Action from U.S. Appl. No. 10/918,825, mailed on Nov. 7, 2005.
Non-Final Office Action from U.S. Appl. No. 11/110,204, mailed on Aug. 5, 2008.
Non-Final Office Action from U.S. Appl. No. 11/110,204, mailed on Feb. 4, 2010.
Non-Final Office Action from U.S. Appl. No. 11/110,204, mailed on Jun. 17, 2009.

(56) References Cited

OTHER PUBLICATIONS

Non-Final Office Action from U.S. Appl. No. 11/129,006, mailed on Dec. 15, 2009.
Non-Final Office Action mailed on Jan. 20, 2012 for U.S. Appl. No. 13/163,597, filed Jun. 17, 2011, 14 pages.
Non-Final Office Action mailed on Oct. 17, 2011 for U.S. Appl. No. 12/732,124, filed Mar. 25, 2010, 8 pages.
Non-Final Office Action from U.S. Appl. No. 11/596,092, mailed on Jun. 10, 2009.
Non-Final Office Action from U.S. Appl. No. 11/884,566, mailed on Aug. 3, 2010.
Non-Final Office Action mailed on Jun. 28, 2011, for U.S. Appl. No. 12/732,124, filed Mar. 25, 2010, 11 pages.
Non-Final Office Action mailed on Aug. 2, 2012 for U.S. Appl. No. 12/575,277, filed Oct. 7, 2009, 8 pages.
Non-Final Office Action mailed on Aug. 7, 2012 for U.S. Appl. No. 12/575,367, filed Oct. 7, 2009, 9 pages.
Non-Final Office Action mailed on Feb. 13, 2013 for U.S. Appl. No. 13/247,962, filed Sep. 28, 2011, 21 pages.
Non-Final Office Action mailed on Mar. 1, 2013 for U.S. Appl. No. 13/399,828, filed Feb. 17, 2012, 6 pages.
Non-Final Office Action mailed on Mar. 25, 2013 for U.S. Appl. No. 13/728,807, filed Dec. 27, 2012, 13 pages.
Notice of Allowance from U.S. Appl. No. 09/841,341, mailed on Oct. 7, 2002.
Notice of Allowance from U.S. Appl. No. 10/027,591, mailed on Jul. 29, 2003.
Notice of Allowance from U.S. Appl. No. 10/337,192, mailed on Mar. 11, 2004.
Notice of Allowance from U.S. Appl. No. 10/697,912, mailed on Dec. 30, 2004.
Notice of Allowance mailed on Nov. 8, 2010, for U.S. Appl. No. 11/110,204, filed Apr. 20, 2005, 6 pages.
Notice of Allowance mailed on Jun. 26, 2012 for U.S. Appl. No. 12/732,124, filed Mar. 25, 2010, 11 pages.
Notice of Allowance mailed on Nov. 13, 2012 for U.S. Appl. No. 12/732,124, filed Mar. 25, 2010, 11 pages.
Notice of Allowance mailed on Feb. 21, 2013 for U.S. Appl. No. 12/575,367, filed Oct. 7, 2009, 5 pages.
Notice of Allowance mailed on May 20, 2013, for U.S. Appl. No. 13/730,276, filed Dec. 28, 2012, 7 pages.
Notice of Reexamination for Chinese Patent Application No. 0811654.X, mailed Nov. 5, 2009; 7 pages.
Notice Regarding Non-Compliant Amendment from U.S. Appl. No. 10/918,803, mailed on Nov. 19, 2009.
Notification of Reasons for Rejection for Japanese Patent Application No. 2003-537642, mailed on May 26, 2009, 4 pages.
Office Action for European Patent Application No. 04 816 855.3, mailed on Oct. 21, 2008, 4 pages.
Office Action for European Patent Application No. 01 928 855.4, mailed on Feb. 26, 2009, 3 pages.
Office Action for European Patent Application No. 01 928 855.4, mailed on Nov. 15, 2007, 4 pages.
Office Action for European Patent Application No. 01 928 855.4, mailed on Mar. 29, 2006, 6 pages.
Office Action for European Patent Application No. 01 928 855.4, mailed on Jul. 13, 2004, 5 pages.
Office Action for European Patent Application No. 02 757 407.8, mailed on Oct. 6, 2009, 3 pages.
Office Action for European Patent Application No. 02 757 407.8, mailed on Jul. 1, 2009, 2 pages.
Office Action for European Patent Application No. 02 757 407.8, mailed on Oct. 21, 2008, 3 pages.
Office Action for European Patent Application No. 02 757 407.8, mailed on Jun. 6, 2007, 2 pages.
Office Action for European Patent Application No. 02 757 407.8, mailed on Jan. 24, 2006, 3 pages.
Office Action for European Patent Application No. 04 816 855.3, mailed on Feb. 2, 2011, 4 pages.
Office Action for European Patent Application No. 05 752 122.1, mailed on Dec. 28, 2010, 4 pages.
Office Action for European Patent Application No. 05 752 122.1, mailed on Mar. 25, 2013, 4 pages.
Office Action for European Patent Application No. 04 810 878.1, mailed on Sep. 10, 2010, 4 pages.
Ohno-Matsui et al., Invest. Ophthalmol. Vis: Sci. (2003) 44:5370-5375.
Okkenhaug et al., Science (2002) 297:1031-1034.
Oppenheimer-Marks et al., J. Clin. Invest. (1998) 101:1261-1272.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Parasharya et al., Chemical Abstracts (1994) vol. 121, No. 9, p. 1065.
Park, S. et al. (2010). "Role of the PI3K/AKT and mTOR Signaling Pathways in Acute Myeloid Leukemia," *Haematologica* 95(5):819-829.
Parker, Current Biology (1995) 5:577-579.
Passegue et al., Proc. Natl. Acad. Sci., (USA) (2003) 100 Supp. 1:11842-11849.
Patani, G.A. et al. (1996), "Bioisosterism: A Rational Approach in Drug Design," *Chem Rev.* 96(8):3147-3176.
Pierce et al., J. Biol. Chem. (1997) 272:21096-21103.
Plows et al., J. Immunol. (1999) 162(2):1018-1023.
Podsypanina et al., Proc. Natl. Acad. Sci. (USA) (2001) 98:10320-10325.
Psychoyos et al., J. Immunol. Methods (1991) 137:37-46.
Puri et al., Blood (2005) 106(1):150-157, 144.
Puri et al., Blood (May 2004) 103:3448-3456.
Puri, K. et al. (Jul. 18-23, 2004). "A Role for Phosphoinositide 3-Kinase δ in Neutrophil Trafficking," Immunology 2004: Cytokine Network, Regulatory Cells, Signaling, and Apoptosis: Collection of Free Papers *Presented at the 12$^{th}$ International Congress of Immunology and 4$^{th}$ Annual Conference of FOCIS Medimond International Proceedings in* Montreal, Canada on Jul. 18, 23, 2004, pp. 303-307.
Quirici et al., Br. J. Haematol. (2001) 115:186-194.
Rameh et al., Cell (1995) 83:821-830.
Rameh et al., J. Biol. Chem. (1999) 274:8347-8350.
Rathman et al., J. Org. Chem. (1980) 45:2169-2176.
Remington's Pharmaceutical Sciences (1990) 18th Ed., Chapter 89, pp. 1435-1712 Table of Contents Only.
Ren et al., Curr. Drug Targets Inflamm. Allergy (2003) 2(3):242-256.
Request for Continued Examination and Amendment Under 37 C.F. R. § 1.116 from U.S. Appl. No. 10/918,803, filed May 7, 2009.
Response to Election of Species Requirement from U.S. Appl. No. 10/918,803, filed Jun. 27, 2007.
Response to Non-Final Office Action from U.S. Appl. No. 10/918,803, filed Dec. 18, 2009.
Response to Non-Final Office Action filed on Sep. 16, 2010, for U.S. Appl. No. 10/918,803, filed Aug. 13, 2004, 25 pages.
Response to Restriction Requirement from U.S. Appl. No. 10/918,803, filed Jan. 4, 2008.
Response to Restriction Requirement from U.S. Appl. No. 11/129,006, filed May 12, 2009.
Response to Restriction Requirement from U.S. Appl. No. 11/137,901, filed Feb. 6, 2008.
Response to Restriction Requirement from U.S. Appl. No. 11/596,092, filed May 27, 2009.
Restriction Requirement from U.S. Appl. No. 10/918,803, mailed on Jun. 12, 2009.
Restriction Requirement from U.S. Appl. No. 10/918,803, mailed on Mar. 13, 2007.
Restriction Requirement from U.S. Appl. No. 10/918,803, mailed on Sep. 7, 2007.

(56) References Cited

OTHER PUBLICATIONS

Restriction Requirement from U.S. Appl. No. 11/110,204, mailed on Mar. 10, 2008.
Restriction Requirement from U.S. Appl. No. 11/129,006, mailed on Nov. 12, 2008.
Restriction Requirement from U.S. Appl. No. 11/137,901, mailed on Aug. 6, 2007.
Restriction Requirement from U.S. Appl. No. 11/137,901, mailed on May 23, 2008.
Restriction Requirement from U.S. Appl. No. 11/596,092, mailed on Jan. 28, 2009.
Restriction Requirement from U.S. Appl. No. 11/884,566, mailed on Apr. 5, 2010.
Restriction Requirement mailed on Oct. 14, 2010, for U.S. Appl. No. 12/732,124, filed Mar. 25, 2010, 9 pages.
Restriction Requirement mailed on Dec. 1, 2011, for U.S. Appl. No. 13/163,597, filed Jun. 17, 2011, 7 pages.
Restriction Requirement mailed on Jun. 7, 2012, for U.S. Appl. No. 13/399,828, filed Feb. 17, 2012, 5 pages.
Restriction Requirement mailed on Jul. 17, 2012, for U.S. Appl. No. 13/247,962, filed Sep. 28, 2011, 27 pages.
Restriction Requirement mailed on Sep. 11, 2012, for U.S. Appl. No. 13/399,828, filed Feb. 17, 2012, 7 pages.
Reyes et al., J. Clin. Invest. (2002) 109:337-346.
Rickert et al., Trends Cell Biol. (2000) 10:466-473.
Riesterer, Int'l J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., EMBO J. (1996) 15:2442-2451.
Roth et al., J. Immunol. Methods (1995) 188:97-116.
Rudd, Immunity (1996) 4:527-534.
Rupnick et al., Proc. Nat'l. Acad. Sci. (USA) (2002) 99:10730-35.
Sadhu et al., J. Immunol. (2003) 170:2647-2654.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schimmer et al., J. Immunol. (1998) 160:1466-1471.
Schuch et al., Blood (2002) 100:4622-4628.
Schueneman et al., Canc. Res. (2003) 63:4009-4016.
Second Preliminary Amendment and Response to Notice to File Missing Parts of Nonprovisional Application from U.S. Appl. No. 12/575,277, filed Jan. 20, 2010.
Second Preliminary Amendment and Response to Notice to File Missing Parts of Nonprovisional Application from U.S. Appl. No. 12/575,367, filed Jan. 20, 2010.
Second Preliminary Amendment from U.S. Appl. No. 11/110,204, filed Aug. 24, 2007.
Second Preliminary Amendment from U.S. Appl. No. 11/884,566, filed May 13, 2008.
Sengupta et al., Circulation (2003) 107:2955-2961.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Song et al., Canc. Res. (1974) 34:2344-2350.
Springer, Cell (1994) 76:301-314.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed Oct. 27, 2009.
Supplemental Notice of Allowance from U.S. Appl. No. 10/337,192, mailed on Jun. 29, 2004.
Tager et al., J. Exp. Med. (2000) 192:439-446.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000), 238:59-68.
Tan, J. et al. (Sep. 1, 2004). "A Specific Antagonist of the p110-Delta Catalytic Component of P13 Kinase, IC486068, Enhances Radiation-Induced Tumor Vascular Destruction," *International Journal of Radiation: Oncology Biology Physics* 60(1):S195.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).
The Merck Manual, 17th ed, (1999) p. 1001.
Thelan et al., Proc. Natl. Acad. Sci. (USA) (1994) 91:4960-4964.
Ting et al., Int. J. Rad. Biol. (1991) 60:335-339.
U.S. Appl. No. 13/765,610, filed Feb. 12, 2013, by Kesicki et al.
Vacca et al., Blood (1999) 9:3064-3073.
Van Dijk et al., Blood (2000) 96:3406-3413.
Vanhaesebroeck et al., FASEB J. (1996) 10:A1395, Abst. No. 2280.
Vanhaesebroeck et al., Proc. Natl. Acad. Sci., (USA) (1997) 94:4330-4335.
Vanhaesebroeck et al., TIBS (1997) 22:267-272.
Vermes et al., J. Immunol. Meth. (1995) 184:39-51.
Vippagunta, S.R. et al. (2001). "Crystalline Solids," Advanced Drug Delivery 48:3-26.
Vivanco et al., Nat. Rev. Cancer (2002) 2:489-501.
Vlahos et al., J. Immunol. (1995) 154:2413-2422.
Volinia et al., EMBO J. (1995) 14:3339-3348.
Volinia et al., Genomics (1994) 24:472-477.
Volinia et al., Oncogene (1992) 7:789-793.
Webb, H.K. et al. (Apr. 2009). "CAL-101, a Potent and Selective Inhibitor of the Class 1 Phosphatidylinositol 3 Kinase (P13K) p110δ Preclinical Summary," Proceedings of the American Association for Cancer Research 50:894-895, Abstract No. #3703.
Wegner et al., Lung (1992) 170:267-279.
Wegner et al., Science (1990) 247:456-459.
Weiner et al., Nat. Cell Biol. (1999) 1:75-81.
Weyand et al., Arthritis & Rheumatism (2000) 43:1041-1048.
Williams, D.A. et al. (2002). Foye's Principles of Medicinal Chemistry Lippincott, Williams & Wilkins, Baltimore MD, Fifth Edition, pp. 50 and 59-61.
Williams, Methods Mol. Med. (2004) 98:207-216.
Williams et al., Chem. Biol. (2010) 17:123-134.
Wolff, ed., Burger's Medicinal Chemistry and Drug Discovery, 5th edition (1996) vol. 1, New York: John Wiley & Sons, pp. 975-977.
Written Opinion mailed on Jan. 21, 2012 for PCT Application No. PCT/US2010/042801, filed on Jul. 21, 2010, 10 pages.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.
Computer Search, Cart Navigator, retrieved from the internet on Mar. 22, 2001, URL: http://www.chemnavigator.com/members/CartNavigator.asp#sample1, 8 pages.
Extended European Search Report dated Jun. 6, 2013 for EP Patent Application No. 13150110.8, filed May 12, 2005, 6 pages.
Final Office Action mailed on Jul. 9, 2013, for U.S. Appl. No. 13/399,828, filed Feb. 17, 2012, 6 pages.
Non-Final Office Action mailed on Jun. 26, 2013 for U.S. Appl. No. 13/765,610, filed Feb. 12, 2013, 9 pages.

(56) References Cited

OTHER PUBLICATIONS

Notice of Allowance mailed on Jul. 8, 2013 for U.S. Appl. No. 13/728,807, filed on Dec. 27, 2012, 9 pages.
Notice of Allowance mailed on Jul. 8, 2013, for U.S. Appl. No. 13/730,256, filed Dec. 28, 2012, 9 pages.
Notice of Allowance mailed on Aug. 28, 2013, for U.S. Appl. No. 12/575,277 filed Oct. 7, 2009, 6 pages.
Notice of Allowance mailed on Sep. 19, 2013, for U.S. Appl. No. 13/399,828 filed Feb. 17, 2012, 6 pages.
Notice of Allowance mailed on Oct. 3, 2013, for U.S. Appl. No. 13/247,962 filed Feb. 28, 2011, 9 pages.
Response to Rule 312 Communication mailed on Oct. 4, 2012, for U.S. Appl. No. 12/732,124, filed Mar. 25, 2010, 7 pages.
U.S. Appl. No. 14/049,154, filed Oct. 8, 2013, by Fowler et al.
U.S. Appl. No. 14/049,163, filed Oct. 8, 2013, by Fowler et al.
Notice of Allowance mailed on Oct. 18, 2013, for U.S. Appl. No. 13/765,610, filed Feb. 12, 2013, 10 pages.

* cited by examiner

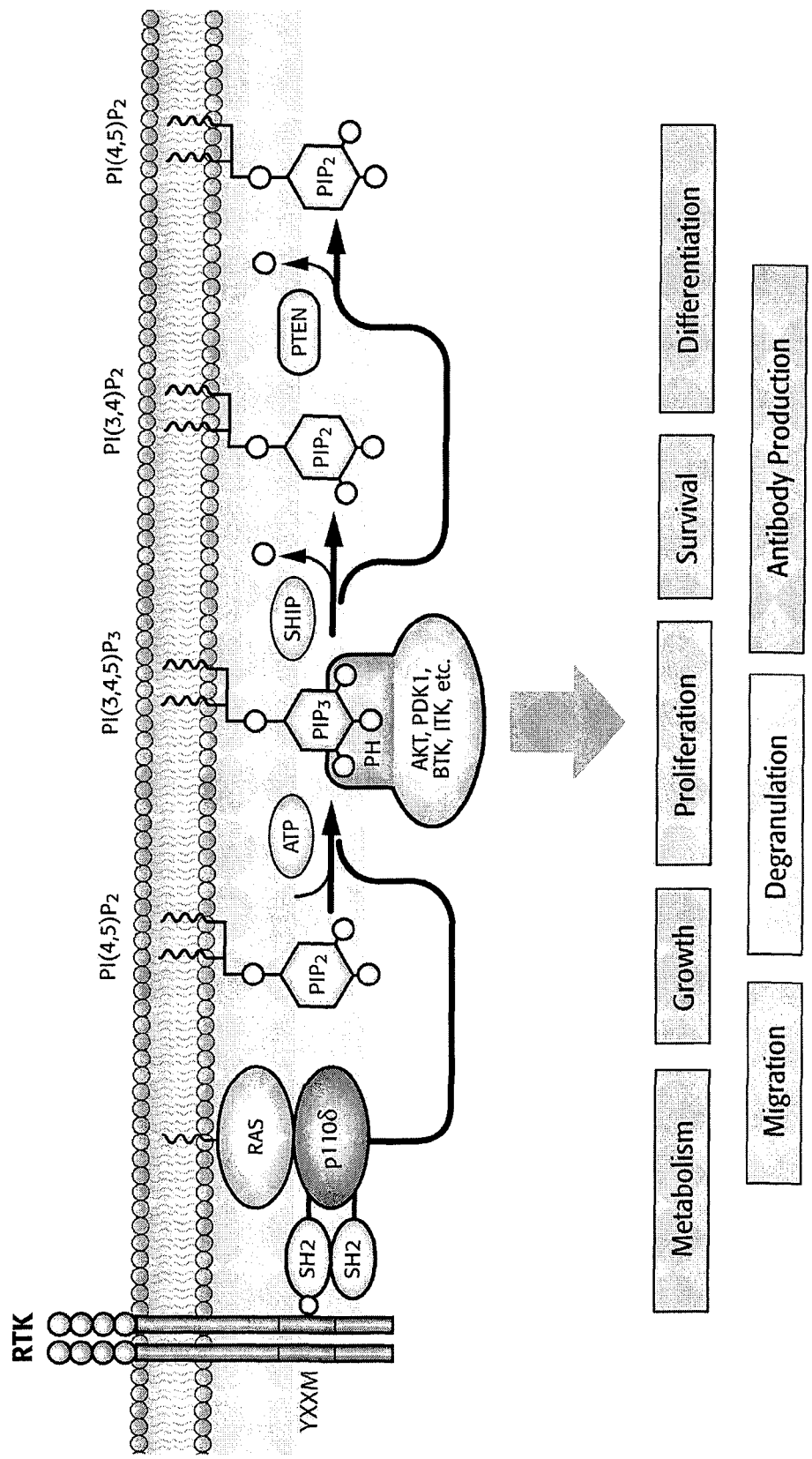

TREATMENT OF LIVER DISORDERS WITH PI3K INHIBITORS

RELATED APPLICATIONS

This application is a National Phase filing under 35 U.S.C. §371 of International Application PCT/US2010/042801, with an International Filing Date of Jul. 12, 2010, entitled "TREATMENT OF LIVER DISORDERS WITH P13K INHIBITORS, which claims priority to U.S. provisional application 61/227,343 filed Jul. 21, 2009. The contents of that provisional application are incorporated herein by reference.

TECHNICAL FIELD

The present invention relates to methods for treating certain liver disorders using compounds that inhibit phosphatidylinositol-3,4,5-triphosphate kinase (PI3K) enzymes in vivo. It provides compounds, compositions and combinations useful for treating a variety of disorders that primarily affect the liver.

BACKGROUND ART

Various phosphorylated forms of phosphatidylinositol are critical regulators of many cell functions, including primary metabolism, growth and proliferation of cells, differentiation, cell migration, immune responses, and apoptosis. Because they are involved in many aspects of cell regulation, it is not always predictable what effect a drug candidate may have when it inhibits conversion of phosphatidylinositol between its various phosphorylated forms. For example, FIG. 1 illustrates some of the known roles played by phosphatidylinositol-4,5-diphosphate (PI-4,5-P2, also referred to herein as PIP2) and phosphatidylinositol-3,4,5-triphosphate (PI-3,4,5-P3, also referred to herein as PIP3). PIP3 activates a number of receptors, some of which are involved in cell growth, replication, and death (apoptosis).

It has recently been reported that the tumor suppressor Pten is mutated in many human cancers, and its expression is reduced or absent in almost half of hepatoma patients. Pten's major substrate is PIP3, which it dephosphorylates to form PIP2. Its strong association with liver cancers in particular suggests that Pten is especially important for maintaining homeostasis and preventing tumor formation in the liver. It has also been shown that hepatocyte-specific Pten deficiency leads to steatohepatitis and hepatic carcinomas. Y. Horie, et al., *J. Clin. Investigation,* 113(12), 1774-83 (2004). Horie concludes that controlled blocking of the PI3K pathway may be beneficial for treatment of patients predisposed to NASH, liver cirrhosis or hepatic carcinomas. It has also been reported recently that steatosis (accumulation of fat) induced by exposure of hepatocytes to conditions that generate reactive oxygen species can be inhibited by LY294002, an inhibitor of kinases that phosphorylate PIP2 to form PIPS. R. Kohli, et al., *J. Biol. Chem.* 282, 21327-36 (July 2007). Kohli demonstrated that LY294002 blocked steatosis development in a model system where diet induced p85 expression and steatosis, demonstrating that an inhibitor of PI3Ks can prevent development of steatosis.

Liver disorders are increasingly common due to high calorie diets and high obesity rates in the developed world. These are risk factors for fatty liver conditions that can progress to cirrhosis. NASH (non-alcoholic steatohepatitis) is one such condition: it was first identified in 1980, but is now a widely recognized condition affecting millions of Americans. Kohli, et al. As many as 30 million Americans are believed to have nonalcoholic fatty liver disease (FALD), and about 30% of those are believed to have NASH. Methods to treat liver disorders associated with excessive fatty deposits are therefore needed. The present invention provides compounds and methods for preventing and/or treating such conditions.

DISCLOSURE OF THE INVENTION

The invention provides compounds useful for the treatment of liver disorders, especially ones wherein Ptenis underexpressed or mutated. Conditions that can be prevented and/or treated according to the invention include, for example, non-alcoholic fatty liver disease (NAFLD), non-alcoholic steatohepatitis (NASH), hepatic steatosis, cirrhosis, hepatitis, liver adenomas, insulin hypersensitivity, and liver cancers such as hepatoma, liver cell adenoma and hepatocellular carcinoma. The invention further provides methods for identifying patients who are most likely to respond to these treatments.

In one aspect, the invention provides a method to treat a subject having a liver disorder, which comprises administering to the subject an effective amount of a compound that inhibits PI3K. Suitable compounds for use in these methods are described herein.

PI3K exists as a heterodimer, combining a p110 unit with a p85 unit, and there are several isoforms of PI3K that contain different p110 and/or p85 subunits. In particular, there are four p110 subunits known, referred to as p110α, p110β, p110γ, and p110δ. Tissue distribution of these varies, with p110α occurring widely; p110β dominating in certain tissues like brain and liver; and p110δ dominating in the spleen and hematopoietic tissues.

In tissues where more than one isoform occurs, it may be desirable to selectively inhibit one particular isoform to achieve a desired therapeutic effect, or it may be desirable to inhibit two of these isoforms, or all of them. Compounds that inhibit all of the isoforms are known, and are referred to as pan-PI3K inhibitors; compounds that selectively inhibit one or two of the isoforms are particularly useful in certain disorders, and offer a reduced likelihood of undesired side effects in tissues other than the one targeted. The methods described herein thus preferably use a selective PI3K inhibitor, such as an inhibitor that is more active against PI3Kβ or PI3Kδ, or both of these isoforms over the others.

In one aspect, the inhibitor of PI3K is a selective that inhibits one isoform of PI3K more effectively than another isoform of PI3K. For treatment of liver disorders, some embodiments of the invention utilize a PI3K inhibitor that is effective against at least PI3Kβ; in some embodiments the inhibitor is selective for inhibition of PI3Kβ relative to PI3Kγ and/or PI3Kα. In certain embodiments, the inhibitor has an IC-50 against PI3Kβ that is less than about 100 nM, and preferably less than about 60 nM.

The methods and compounds described herein can be used to combat the effects of insufficient Pten activity, by restoring a normal 'balance' of PIP3 and PIP2. In one embodiment, the methods of the invention can be monitored by assessing levels of PIP2 in the subject, or by assessing the ratio of PIP2 to PIP3 and adjusting dosage of a compound of the invention to produce a ratio within the normal range for similar subjects.

In one aspect, the PI3K inhibitor is a substituted pyrimidine: suitable compounds are described in WO 2007/12175; WO 2007/042810; WO 2007/132171; WO 2007/129161; WO 2006/046031; and WO 2009/070524. Preferably, the pyrimidine compound exhibits an IC-50 against PI3Kβ that is less than about 100 nM, and preferably less than about 60 nM.

In another aspect, the PI3K inhibitor is a quinazolinone compound such as those disclosed in U.S. Pat. Nos. 6,518,277 or 6,667,300, which are incorporated herein by reference for their disclosures of specific quinazolinone compounds and methods of making such compounds. Preferably, the quinazolinone compound exhibits an IC-50 against PI3Kβ that is less than about 100 nM, and preferably less than about 60 nM.

In one aspect, the PI3K inhibitor is a compound of formula (1):

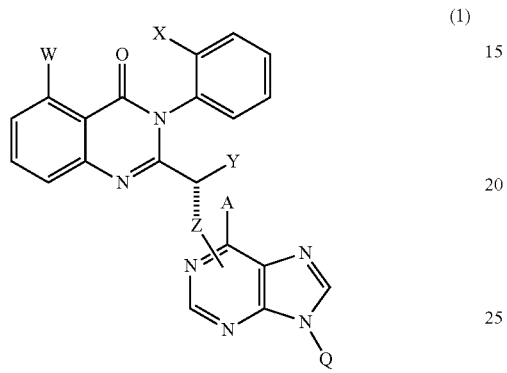

(1)

wherein:
W is selected from the group consisting of H, Me, Cl, and F;
X is selected from the group consisting of H, Me, Cl, and F;
Y is selected from the group consisting of H, Me and Et;
Z is NH or a bond; and
A is $NH_2$, or A is absent and indicates the point of attachment of Z to the purine ring;
Q is H when A is absent, or Q is absent and indicates the point of attachment of Z to the purine ring when A is $NH_2$;
provided that not more than two of W, X, and Y represents H; or a pharmaceutically acceptable salt thereof.

Selected embodiments of the compounds of Formula (1) that are particularly useful in the present methods include compounds of formula (2a) and (2b):

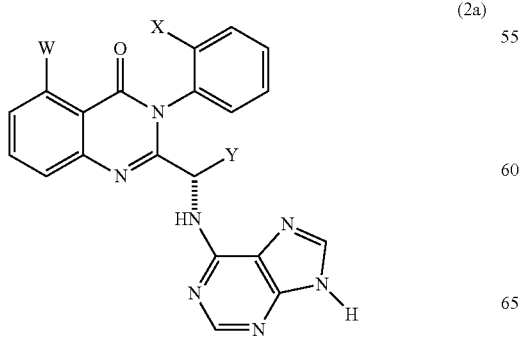

(2a)

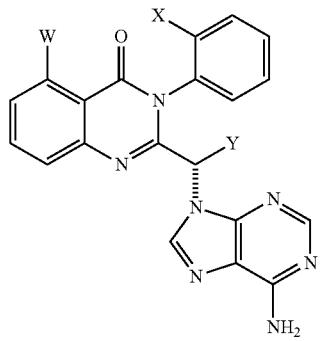

(2b)

wherein W, X and Y are as defined for formula (1), and wherein not more than two of W, X and Y represent H. In certain embodiments, Y is Me or Et.

In another aspect, the methods of the invention can utilize as the PI3K inhibitor a compound of formula (3):

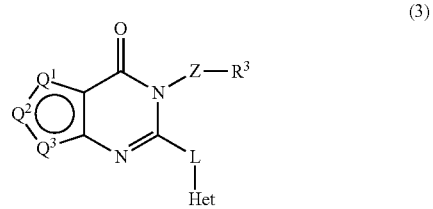

(3)

wherein:
one of $Q^1$, $Q^2$ and $Q^3$ is S, and the other of two of $Q^1$, $Q^2$ and $Q^3$ are $-CR^1-$;
wherein each $R^1$ is independently H, halo, OR, $NR_2$, NROR, $NRNR_2$, SR, SOR, $SO_2R$, $SO_2NR_2$, $NRSO_2R$, $NRCONR_2$, NRCOOR, NRCOR, $CF_3$, CN, COOR, $CONR_2$, OOCR, COR, or $NO_2$,
or $R^1$ can be an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, and C6-C12 heteroarylalkyl groups,
wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
and wherein two R on the same atom or on adjacent atoms can be linked to form a 3-8 membered ring, optionally containing one or two N, O or S as ring members;
and wherein each R group other than H, and each ring formed by linking two R groups together, is optionally substituted;
Z is a bond, or is O, $NR^2$, C1-C6 alkylene or C1-C6 heteroalkylene, each of which is optionally substituted with up to two C1-C6 alkyl or C2-C6 heteroalkyl groups, where two of said alkyl or heteroalkyl groups can optionally cyclize to form a 3-7 membered ring containing up to two heteroatoms selected from O, N and S as ring members;

R³ is aryl, heteroaryl, cycloalkyl, or heterocycloalkyl, each of which is optionally substituted with up to three R¹, or R³ can be H if Z is not a bond;

L is selected from the group consisting of —C(R²)₂—, —C(R²)₂—C(R²)₂—, —C(R²)₂—NR²—, and —C(R²)₂—S(O)ₙ—,
  wherein each R² is independently H or an optionally substituted member selected from C1-C6 alkyl, C2-C6 heteroalkyl, C2-C6 alkenyl, and C2-C6 alkynyl, and n is 0-2;
  and two R², if present on L, can cyclize to form a 3-7 membered ring that may contain up to two heteroatoms selected from N, O and S as ring members;

Het is a monocyclic or bicyclic ring system wherein at least two ring atoms are N and wherein at least one ring is aromatic, and Het is optionally substituted with up to three substituents selected from R⁴, N(R4)₂, S(O)$_p$R⁴, OR⁴, halo, CF₃, CN, NR⁴OR⁴, NR⁴N(R⁴)₂, SR⁴, SOR⁴, SO₂R⁴, SO₂N(R⁴)₂, NR⁴SO₂R⁴, NR⁴CON(R⁴)₂, NR⁴COOR⁴, NR⁴COR⁴, CN, COOR⁴, CON(R⁴)₂, OOCR⁴, COR⁴, or NO₂,
  wherein each R⁴ is independently H or an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, and C6-C12 heteroarylalkyl,
  and wherein two R⁴ on the same atom or on adjacent atoms can be linked to form a 3-8 membered ring, optionally containing one or two heteroatoms selected from N, O and S;
  wherein the optional substituents on each optionally substituted alkyl, heteroalkyl, alkenyl, heteroalkenyl, alkynyl, heteroalkynyl, acyl, heteroacyl, aryl, heteroaryl, arylalkyl and heteroarylalkyl are selected from C1-C4 alkyl, halo, CF₃, CN, =O, =N—CN, =N—OR', =NR', OR', NR'₂, SR', SO₂R', SO₂NR'₂, NR'SO₂R', NR'CONR'₂, NR'COOR', NR'COR', CN, COOR', CONR'₂, OOCR', COR', and NO₂,
  wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;
  and wherein two R' on the same or adjacent atoms can be linked to form a 3-7 membered ring optionally containing up to three heteroatoms selected from N, O and S; and
  p is 0-2;

or a pharmaceutically acceptable salt thereof. Specific embodiments of such compounds are further described below.

In some embodiments, the selective inhibitor is a compound that selectively inhibits PI3Kδ, relative to its inhibition of PI3Kγ. In some embodiments, the selective inhibitor is a compound that selectively inhibits PI3Kδ, relative to its inhibition of PI3Kβ. In some embodiments, the selective inhibitor is a compound that selectively inhibits PI3Kδ, relative to its inhibition of PI3Kα. In some embodiments, the selective inhibitor is a compound that selectively inhibits PI3Kβ, relative to its inhibition of PI3Kγ. In some embodiments, the selective inhibitor is a compound that selectively inhibits PI3Kβ, relative to its inhibition of PI3Kα. In some embodiments, the selective inhibitor is a compound that selectively inhibits PI3Kβ and PI3Kδ relative to its inhibition of either PI3Kα or PI3Kγ.

In some embodiments, the compound is selective for PI3Kδ relative to both PI3Kγ and PI3Kα. In other embodiments, the compound is selective for PI3Kβ relative to both PI3Kα and PI3Kγ. In some embodiments, the compound is selective for PI3Kδ and PI3Kβ relative to both PI3Kα and PI3Kγ.

BRIEF DESCRIPTION OF THE DRAWINGS

FIG. 1 depicts some of the cellular pathways in which phosphatidylinositol phosphate species are known to participate.

MODES OF CARRYING OUT THE INVENTION

Unless otherwise defined herein, terms used herein take their ordinary meaning in the art.

As used herein, the term "alkyl" is defined as straight chained and/or branched hydrocarbon groups containing the indicated number of carbon atoms and an open valence by which the alkyl group is attached to a base molecule; typical examples include methyl, ethyl, and straight chain and branched propyl and butyl groups. The hydrocarbon group can contain up to 16 carbon atoms, unless otherwise specified, and often contain one to eight carbon atoms. The term "alkyl" includes cycloalkyl and "bridged alkyl," i.e., a C6-C16 bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic C3-C8 hydrocarbon group, e.g., cyclopropyl, cyclobutyl, cyclohexyl, and cyclopentyl.

The term "alkenyl" is defined identically as "alkyl," except the alkenyl group contains at least one carbon-carbon double bond, and as a result, the minimum size for an alkenyl group is C2. "Alkynyl" is defined similarly, except that an alkynyl group contains at least one carbon-carbon triple bond.

"Cycloalkenyl" is defined similarly to cycloalkyl, except at least one carbon-carbon double bond is present in the ring.

The term "alkylene" is defined as an alkyl group having a second open valence to which another group is attached, i.e., an alkylene must connect two other substructures. For example, the term "aryl-C1-C3-alkylene" refers to an alkylene group containing one to three carbon atoms, and substituted at one valence with an aryl group, which leaves one remaining valence of the alkylene portion of the group as the point at which it is connected to a base molecule.

The terms "heteroalkyl", "heteroalkenyl", "heteroalkynyl", and "heteroalkylene" as used herein are defined similarly to the terms alkyl, alkenyl, alkynyl and alkylene, except that the tetero' forms include at least one heteroatom selected from N, O and S as a replacement for one of the carbons of the corresponding alkyl, alkenyl, alkynyl or alkylene moiety. In these heteroforms, S can be further oxidized to S=O or —SO₂—, i.e., it can have one or more =O substituents. These groups include at least one carbon atom, and are typically linked to a base molecule through carbon rather than by the heteroatom. Examples of heteroalkyl include methoxymethyl and dimethylaminoethyl, for example, and —CH₂—SO₂—CH₂— is an example of a heteroalkylene.

The term "halo" or "halogen" is defined herein to include fluorine, bromine, chlorine, and iodine. Frequently, fluoro or chloro is preferred in the compounds of formula (1) and (2).

The term "aryl," alone or in combination, is defined herein as a monocyclic or polycyclic aromatic group, e.g., phenyl or naphthyl. Unless otherwise indicated, an "aryl" group can be unsubstituted or substituted, for example, with one or more, and in particular one to three substituents. Preferred substituents for the aryl groups of the invention include halo, alkyl, phenyl, hydroxyalkyl, alkoxy, alkoxyalkyl, haloalkyl, nitro, and amino. Exemplary aryl groups include phenyl, naphthyl, biphenyl, tetrahydronaphthyl, chlorophenyl, fluorophenyl, aminophenyl, methylphenyl, methoxyphenyl, trifluoromethylphenyl, nitrophenyl, carboxyphenyl, and the like. Fluoro, chloro, $CF_3$, CN, methyl, methoxy, dimethylamino, amino, and amine-substituted alkyl and heteroalkyl groups are typical examples suitable as substituents for an aryl ring, whether it is a single ring or is fused to another aryl, nonaryl, or heteroaryl ring.

The term "heteroaryl" is defined herein as a monocyclic or bicyclic ring system containing one or two aromatic rings and containing at least one nitrogen, oxygen, or sulfur atom as a ring member of an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, and amino. F, Cl, $NH_2$, MeNH (methylamine), OMe, Me, and $CF_3$ as well as amine-substituted alkyl or heteroalkyl groups are often preferred substituents for the heteroaryl groups of the invention. Examples of heteroaryl groups include thienyl, furyl, pyridyl, oxazolyl, quinolyl, isoquinolyl, indolyl, triazolyl, isothiazolyl, isoxazolyl, imidazolyl, benzothiazolyl, pyrazinyl, pyrimidinyl, thiazolyl, and thiadiazolyl.

As used herein, the term "amount effective" or "effective amount" means a dosage sufficient to produce a desired or stated effect.

"Treating" as used herein refers to preventing a disorder from occurring in an animal that can be predisposed to the disorder, but has not yet been diagnosed as having it; inhibiting the disorder, i.e., arresting its development; relieving the disorder, i.e., causing its regression; or ameliorating the disorder, i.e., reducing the severity of symptoms associated with the disorder.

"Disorder" is intended to encompass medical disorders, diseases, conditions, syndromes, and the like, without limitation.

In one aspect, the PI3K inhibitor is a compound of formula (1a) or (1b):

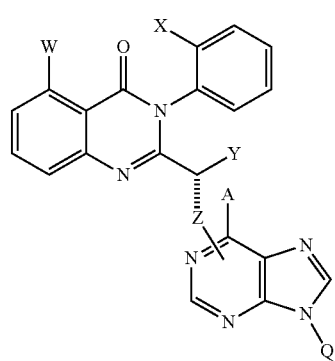

(1a)

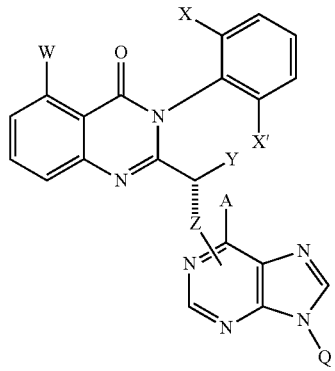

(1b)

wherein:
W is selected from the group consisting of H, Me, Cl, and F;
X and X' are independently selected from the group consisting of H, Me, Cl, and F;
Y is selected from the group consisting of H, Me and Et;
Z is NH or a bond; and
A is $NH_2$, or A is absent and indicates the point of attachment of Z to the purine ring;
Q is H when A is absent, or Q is absent and indicates the point of attachment of Z to the purine ring when A is $NH_2$;
provided that not more than two of W, X, and Y represents H;
or a pharmaceutically acceptable salt thereof.

In some embodiments of the compounds of formula (1a), not more than one of W, X, and Y represents H.

In some embodiments of formula (1a) and (1b), A is absent and the atom it appears to be connected to in the purine ring of formula (1a) or (1b) is actually connected to Z. In these embodiments, Q represents H, and Z is often NH.

In some embodiments, Q is absent and the atom it appears to be connected to in the purine ring of formula (1) is actually connected to Z. In these embodiments, A represents H, and Z is often a bond, i.e., the nitrogen atom on which Q is depicted in formula (1) is directly bonded to the carbon atom to which Y is attached.

In some embodiments of the compounds described above, at least one of W, X, and Y is methyl (Me). In some embodiments, W is Me. In some embodiments, X is Me. In some embodiments, Y is Me.

In some embodiments of the compounds described above, X is H, Me or F.

In some embodiments of the compounds described above, Z is NH.

In some embodiments of the compounds described above, Z is a bond.

In some embodiments of the compounds described above, Y is H.

In some embodiments of the compounds described above, Y is Me.

In some embodiments of the compounds described above, Y is Et.

In some of the embodiments of formula (1b), X and X' are the same. In some such embodiments, they each represent a group other than H. In specific examples of such compounds, X and X' each represent F.

Selected embodiments of the compounds of Formula (1) that are particularly useful in the present methods include compounds of formula (2a) and (2b):

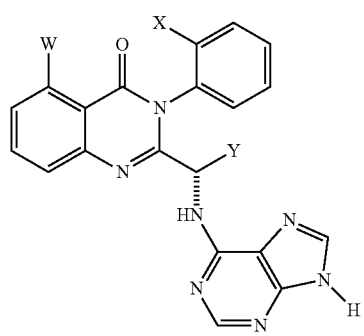

(2a)

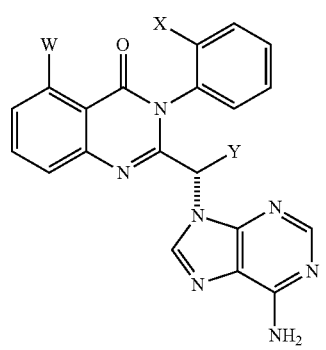

(2b)

wherein W, X and Y are as defined for formula (1), and wherein not more than two of W, X and Y represent H.

In some embodiments of the compounds of formula (2a) and (2b), Y is H, Me or Et. Preferably, Y is Me or Et.

In some of these embodiments of compounds of formula (2a) and (2b), W is H, Me, Cl or F: in formula (2a), W is sometimes F or Me, and in formula (2b), W is sometimes Me or F.

In some of these embodiments of compounds of formula (2a) and (2b), X is H, Me, Cl or F: in formula (2a), X is sometimes F or H, and in formula (2b), X is sometimes Me or H.

Certain compounds of Formula (1a) and (1b) are selective for PI3Kδ or PI3Kβ or both.

Some specific compounds of this type that are particularly useful in the methods described herein include:

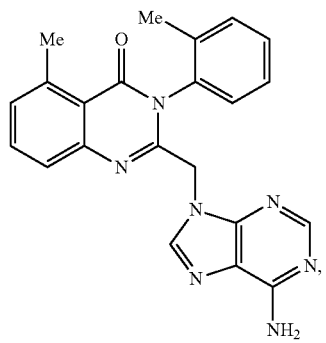

(2c)

including its separable atropisomers, (2c') and (2c"):

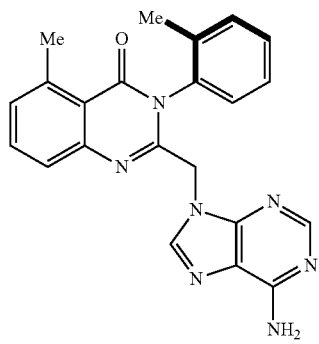

(2c')

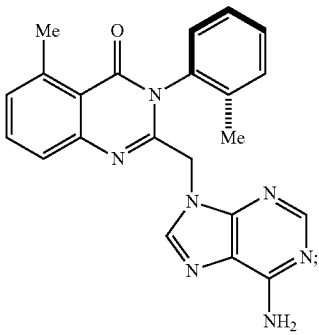

(2c")

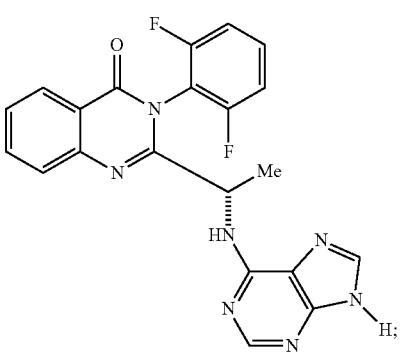

(2d)

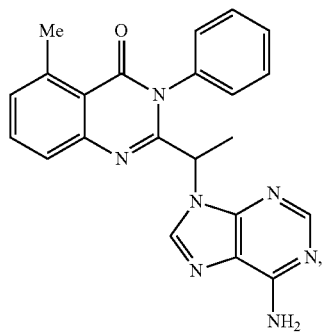

(4a)

including the R and S isomers of the chiral center between the two bicyclic groups, and particularly the S isomer;

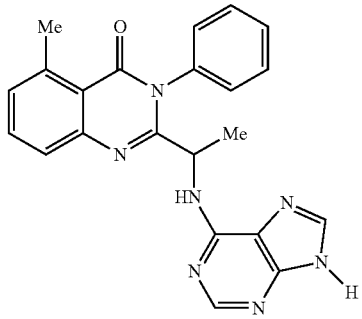

(4b)

including the R and S isomers of the chiral center between the two bicyclic groups, and particularly the S isomer.

In another aspect, the methods of the invention can utilize as the PI3K inhibitor a compound of formula (3):

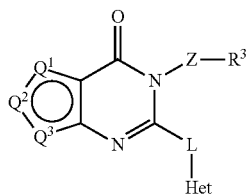

(3)

wherein:
one of $Q^1$, $Q^2$ and $Q^3$ is S, and the other of two of $Q^1$, $Q^2$ and $Q^3$ are —$CR^1$—;
wherein each $R^1$ is independently H, halo, OR, $NR_2$, NROR, $NRNR_2$, SR, SOR, $SO_2R$, $SO_2NR_2$, $NRSO_2R$, $NRCONR_2$, NRCOOR, NRCOR, $CF_3$, CN, COOK, $CONR_2$, OOCR, COR, or $NO_2$,
or $R^1$ can be an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, and C6-C12 heteroarylalkyl groups,
wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
and wherein two R on the same atom or on adjacent atoms can be linked to form a 3-8 membered ring, optionally containing one or two N, O or S as ring members;
and wherein each R group other than H, and each ring formed by linking two R groups together, is optionally substituted;
Z is a bond, or is O, $NR^2$, C1-C6 alkylene or C1-C6 heteroalkylene, each of which is optionally substituted with up to two C1-C6 alkyl or C2-C6 heteroalkyl groups, where two of said alkyl or heteroalkyl groups can optionally cyclize to form a 3-7 membered ring containing up to two heteroatoms selected from O, N and S as ring members;

$R^3$ is aryl, heteroaryl, cycloalkyl, or heterocycloalkyl, each of which is optionally substituted with up to three $R^1$, or $R^3$ can be H if Z is not a bond;
L is selected from the group consisting of —$C(R^2)_2$—, —$C(R^2)_2$—$C(R^2)_2$—, —$C(R^2)_2$—$NR^2$—, and —$C(R^2)_2$—$S(O)_n$—,
wherein each $R^2$ is independently H or an optionally substituted member selected from C1-C6 alkyl, C2-C6 heteroalkyl, C2-C6 alkenyl, and C2-C6 alkynyl, and n is 0-2;
and two $R^2$, if present on L, can cyclize to form a 3-7 membered ring that may contain up to two heteroatoms selected from N, O and S as ring members;
Het is a monocyclic or bicyclic ring system wherein at least two ring atoms are N and wherein at least one ring is aromatic, and Het is optionally substituted with up to three substituents selected from $R^4$, $N(R^4)_2$, $S(O)_pR^4$, $OR^4$, halo, $CF_3$, CN, $NR^4OR^4$, $NR^4N(R^4)_2$, $SR^4$, $SOR^4$, $SO_2R^4$, $SO_2N(R^4)_2$, $NR^4SO_2R^4$, $NR^4CON(R^4)_2$, $NR^4COOR^4$, $NR^4COR^4$, CN, $COOR^4$, $CON(R^4)_2$, $OOCR^4$, $COR^4$, or $NO_2$,
wherein each $R^4$ is independently H or an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, and C6-C12 heteroarylalkyl,
and wherein two $R^4$ on the same atom or on adjacent atoms can be linked to form a 3-8 membered ring, optionally containing one or two heteroatoms selected from N, O and S;
wherein the optional substituents on each optionally substituted alkyl, heteroalkyl, alkenyl, heteroalkenyl, alkynyl, heteroalkynyl, acyl, heteroacyl, aryl, heteroaryl, arylalkyl and heteroarylalkyl are selected from C1-C4 alkyl, halo, $CF_3$, CN, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$,
wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;
and wherein two R' on the same or adjacent atoms can be linked to form a 3-7 membered ring optionally containing up to three heteroatoms selected from N, O and S; and
p is 0-2;
or a pharmaceutically acceptable salt thereof.

In certain embodiments of the compounds of formula (3), $Q^1$ is S and $Q^2$ and $Q^3$ each represent $CR^1$. In other embodiments of the compounds of formula (3), $Q^2$ is S and $Q^1$ and $Q^3$ each represent $CR^1$. In still other embodiments, $Q^3$ is S and $Q^1$ and $Q^2$ each represent $CR^1$. At least one of $Q^1$, $Q^2$ and $Q^3$ is often CH, and in some of these embodiments, two of them are CH. Where $R^1$ in $Q^1$, $Q^2$ or $Q^3$ is other than H, it is frequently C1-C4 alkyl, $CF_3$, CN, or halo, or it may be an amine-substituted alkyl or heteroalkyl group as described below.

In some embodiments of the compounds of formula (3), $R^1$ on the thiophene ring represents an amine-substituted alkyl or heteroalkyl group such as —$(CH_2)_p$—$NR'_2$ or —O—$(CH_2)_p$—$NR'_2$ or —NR'—$(CH_2)_p$—$N(R')_2$, wherein p is 1-4 and each R' is H or C1-C4 alkyl, and wherein two R' present on one N may cyclize to form a 3-8 membered ring, which can optionally include an additional heteroatom selected from N, O and S, specific examples of these amine-substituted alkyl and heteroalkyl groups include, without limitation:

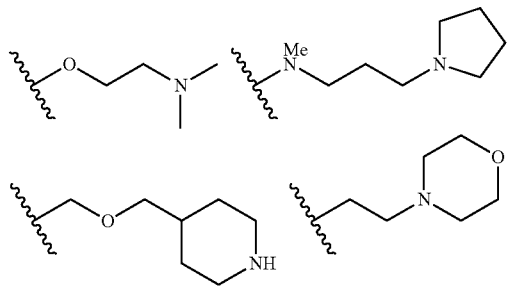

In some embodiments of the compounds of formula (3), Z represents a bond; in other embodiments, it represents $(CH_2)_{1-4}$. Where Z is a bond, $R^3$ often represents an aryl or heteroaryl ring; in some of these embodiments, $R^3$ is an optionally substituted phenyl or pyridyl ring. In these embodiments, $R^3$ is often substituted with at least one substituent, which is frequently ortho or meta to the point of attachment of the aryl ring to Z. In some of these embodiments, $R^3$ is substituted with 1-3 substituents such as halo, CN, methyl, $CF_3$, or an amine-substituted alkyl or heteroalkyl as described above for $R^1$. When Z is a bond, $R^3$ is frequently phenyl, halo-substituted phenyl, dihalo phenyl, or cyanophenyl. In other embodiments, Z is a bond or $(CH_2)_{1-2}$, and $R^3$ represents a cycloalkyl group, which can be substituted.

In some preferred embodiments of the compounds of formula (3), L is $C(R^2)_2$ or $C(R^2)_2NH$ or $C(R^2)_2S$, where each $R^2$ is independently H or C1-C4 alkyl, C2-C4 alkenyl or C2-C4 alkynyl. In certain embodiments, L is $CH(R^2)$ or $CH(R^2)NH$ or $CH(R^2)S$, where $R^2$ represents methyl or ethyl or any optionally substituted C1-C6 alkyl group, or $R^2$ can be an amine-substituted alkyl group as described above for $R^1$. Where one terminus of L is a heteroatom, L is often linked to Het via this heteroatom; and the heteroatom of L is typically attached to a carbon atom of Het.

In many embodiments of the compounds of formula (3), the center $CH(R^2)$ of the linker "L" is chiral, and frequently the S enantiomer of this stereocenter is preferred. In other embodiments, this stereocenter is an R enantiomer. Typically, where L is $CH(R^2)NH$ or $CH(R^2)S$, the N or S is linked to Het, and $CH(R^2)$ is directly bonded to the pyrimidinone ring. In still other embodiments, L is —$CH(R^2)$—$NR^2$—, wherein the two $R^2$ groups are linked to form a ring, which is often a 5-6 atom ring. In these cyclic linkers, a chiral center is also present at $CH(R^2)$, and that center may be in either the R or S configuration; the S enantiomer is often preferred. An exemplary ring for such cyclic linkers is pyrrolidine.

Het is an optionally substituted monocyclic or bicyclic ring, and at least one ring of Het is typically a heteroaryl ring containing at least two nitrogen atoms as ring members; in many embodiments, Het is a bicyclic aromatic heterocycle. In certain embodiments of the compounds of formula (3), Het represents a purine ring, which may be substituted with a C1-C4 alkyl group, C6-C10 aryl group, C5-C10 heteroaryl group, halo, amine, alkylamine, dialkylamine, or an amine-substituted alkyl or heteroalkyl group as described above for $R^1$. In other embodiments, Het represents a pyrazolopyrimidine or a pyrrolopyrimidine ring, each of which can be similarly substituted. In still other embodiments, Het represents a pyrimidine or triazine ring, which can also be similarly substituted.

Where Het represents a bicyclic group, it can be attached to L at any available ring position of Het. In many embodiments, L is attached to a carbon or nitrogen atom that is adjacent to an atom shared by both rings of the bicyclic group. In many embodiments, Het represents a 6,5-bicyclic heteroaromatic group, and L may be attached to either the 5-membered ring or the 6-membered ring. In some embodiments, Het is a purine ring, for which the following atom numbering convention is used:

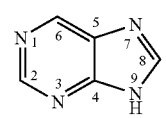

Some specific examples of Het, without limiting its scope, include the following, where [L] indicates the point at which Het is attached to linker "L", and —X represents a preferred point of attachment for a substituent when one is present. In some embodiments, no substituents other than H are present (each X represents H); in others where more than one X is shown, at least one X is H. In many embodiments, each X that is not H represents an amine or substituted amine, an alkyl or aryl group, or a halogen. Some preferred groups for X include $NH_2$, F, Cl, Me, $CF_3$, and phenyl.

Where L in the compounds of formula (3) is attached at N-9 of a purine or purine analog (using the purine numbering scheme for simplicity, even when the ring is a purine analog), such as the heterocycles depicted below, L represents $CH_2$ or $CH(R^2)$. Where L is attached to C-6 of a purine or purine analog such as the heterocycles depicted here, L is frequently $CH(R^2)$—NH, $CH(R^2)$—S or $CH(R^2)$—$N(R^2)$, and the heterocycle represented by Het is typically linked to the heteroatom of L in these embodiments. In many of these embodiments, $R^2$ on a carbon atom of the linker L is methyl or ethyl, and when $R^2$ is on nitrogen of the linker, it is often H.

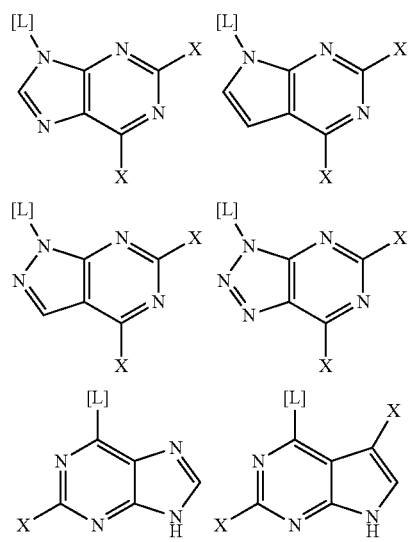

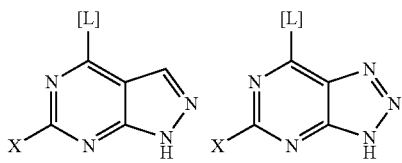

In some preferred embodiments of the compound of formula (3), $R^3$ represents optionally substituted phenyl and Z is a bond. Particularly preferred phenyl groups include unsubstituted phenyl, 2-methylphenyl, 3-methylphenyl, 4-methylphenyl, 2-methoxyphenyl, 3-methoxyphenyl, 4-methoxyphenyl, 2-fluorophenyl, 3-fluorophenyl, 4-fluorophenyl, 2,3-difluorophenyl, 2,5-difluorophenyl, 2,4-difluorophenyl, 3,4-difluorophenyl, 3,5-difluorophenyl, and 2,6-difluorophenyl.

In some preferred embodiments of the compounds of formula (3), -L-Het represents —CH₂-Het, —CH₂-NH-Het, —CH₂-S-Het, —CHMe-Het, —CHMe-S-Het, —CHMe-NH-Het, —CHEt-Het, —CHEt-S-Het, or —CHEt-NH-Het.

In some preferred embodiments of the compounds of formula (3), Het represents a purine that is linked to L at position 6. In other preferred embodiments, when -L-Het is —CH₂-Het, —CHMe-Het, or —CHEt-Het, Het is purine that is linked to L at position 9 of the purine. When Het is a purine ring, it is sometimes substituted by amino, fluoro, methyl or CF₃; and sometimes it is unsubstituted. In other preferred embodiments, Het is a pyrazolopyrimidine and is linked to L at a position that corresponds to position 6 or position 9 of the purine ring, when the pyrimidine rings of the pyrazolopyrimidine and purine are overlaid for purposes of labeling the ring positions.

Compounds of formula (3) having any combination of the preferred features described above are sometimes particularly preferred.

In specific embodiments, the PI3K inhibitor may be a compound having formula (3a) or (3b) or (3c) or a pharmaceutically acceptable salt or solvate thereof:

(3a)

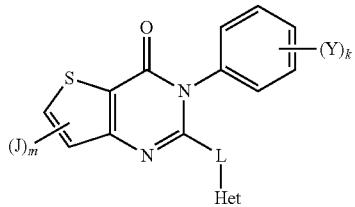

OR (3b)

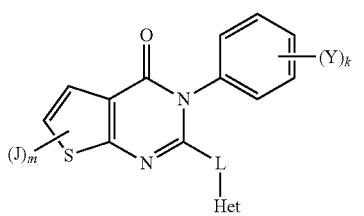

OR (3c)

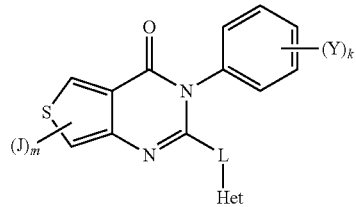

wherein:
each J and each Y is independently selected from the group consisting of F, Cl, Br, CN, Me, CF₃, OMe, CONR²₂, COOR², NMe₂, NH₂, NHMe, -Q-(CH₂)$_q$—OR², and -Q-(CH₂)$_q$—N(R²)₂, where q is 0-4, and Q is absent or is selected from O, S and NR²;
m is 0-2, and k is 0-3;
L is selected from —C(R²)₂—C(R²)₂—NR²—, and —C(R²)₂—S—,
each R² is independently H or an optionally substituted C1-C4 alkyl, C2-C4 alkenyl, or C2-C4 alkynyl, or an optionally substituted C2-C4 heteroalkyl;
and two R², if present on a single atom or on adjacent atoms, can cyclize to form a 3-7 membered ring that is optionally substituted and may contain up to two heteroatoms selected from N, O and S as ring members;
Het is selected from the group consisting of:

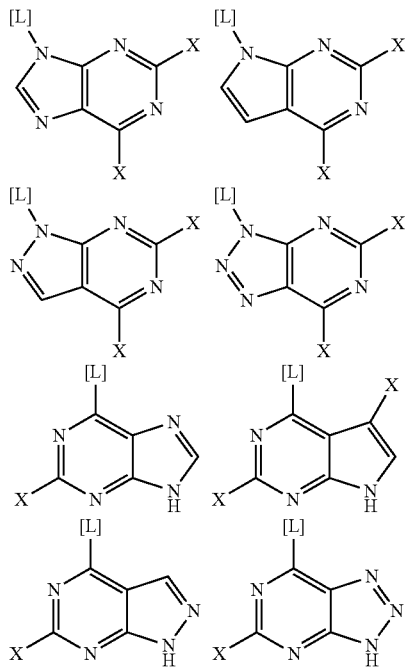

wherein [L] indicates the atom of Het to which L is attached; and
each X is independently H, F, Cl, Br, Me, CF₃, OH, OMe, NH₂, NHAc, or NHMe;
and the optional substituents on each optionally substituted alkyl, heteroalkyl, alkenyl, heteroalkenyl, alkynyl, heteroalkynyl, acyl, heteroacyl, aryl, heteroaryl, arylalkyl and heteroarylalkyl are selected from C1-C4 alkyl, halo, =O, =N—CN, =N—OR', =NR', OR', NR'₂, SR', SO₂R', SO₂NR'₂, NR'SO₂R', NR'CONR'₂, NR'COOR', NR'COR', CN, COOR', CONR'₂, OOCR', COR', and NO₂, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' on the same or adjacent atoms can be linked to form a 3-7 membered ring optionally containing up to three heteroatoms selected from N, O and S;

and p is 0-2;

or a pharmaceutically acceptable salt thereof.

The compounds of formula (3), which includes formula (3a) and formula (3b) and formula (3c), are preferred compounds within the scope of the invention. Particularly preferred are compounds of any one of these formulas that are selective inhibitors of PI3Kβ and/or PI3Kδ. In these compounds, m is frequently 0 or 1, and J, if present, is frequently F, Cl or $CF_3$. Each Y is independently selected, and at least one Y often represents Me, OMe, CN, $CF_3$, or halo. In certain embodiments, Y is F, Me or CN. Each X for the Het group in formula (3) is independently selected, and frequently each X is H, F, Cl, Me, $CF_3$, phenyl, or $NH_2$.

In some preferred embodiments of the compound of formula (3), the phenyl ring shown is an selected from unsubstituted phenyl, 2-methylphenyl, 3-methylphenyl, 4-methylphenyl, 2-methoxyphenyl, 3-methoxyphenyl, 4-methoxyphenyl, 2-fluorophenyl, 3-fluorophenyl, 4-fluorophenyl, 2,3-difluorophenyl, 2,5-difluorophenyl, 2,4-difluorophenyl, 3,4-difluorophenyl, 3,5-difluorophenyl, and 2,6-difluorophenyl.

In some preferred embodiments of the compounds of formula (3), -L-Het represents —$CH_2$-Het, —$CH_2$—NH-Het, —$CH_2$—S-Het, —CHMe-Het, —CHMe-S-Het, —CHMe-NH-Het, —CHEt-Het, —CHEt-S-Het, or —CHEt-NH-Het.

In some preferred embodiments of the compounds of formula (3), Het represents a purine that is linked to L at position 6. In other preferred embodiments, when -L-Het is —$CH_2$-Het, —CHMe-Het, or —CHEt-Het, Het is purine that is linked to L at position 9 of the purine. When Het is a purine ring, it is sometimes unsubstituted, and it is sometimes substituted by amino, fluoro, aryl, methyl or $CF_3$; and sometimes it is unsubstituted. In other preferred embodiments, Het is a pyrazolopyrimidine and is linked to L at a position that corresponds to position 6 or position 9 of the purine ring, when the pyrimidine rings of the pyrazolopyrimidine and purine are overlaid for purposes of labeling the ring positions.

In certain embodiments, the compounds and methods include PI3Kβ or PI3Kδ selective inhibitors of formula (3) containing an amine-substituted alkyl or heteroalkyl group that improves solubility properties, such as by providing for formation of salts. This amine-substituted alkyl or heteroalkyl group may be attached to any of part of these compounds, including Het or the linker "L" in formula (3), or it may be on Z or $R^3$ in formula (3). The amine-substituted groups provide improved solubility characteristics for these compounds, and thus improve their pharmacokinetic properties without adversely affecting their selectivity for the delta isoform of PI3K. Suitable amine-substituted groups that may be present as substituents on the compounds of the invention include —$(CH_2)_p$—NR'$_2$ and —O—$(CH_2)_p$—NR'$_2$, wherein p is 1-4 and each R' is H or C1-C4 alkyl (frequently Me), and wherein two R' present on one N may cyclize to form a 3-8 membered ring, which can optionally include an additional heteroatom such as N, O or S.

The compounds of formula (3) are readily prepared from available starting material using methods that are known in the art. Examples of methods for constructing the thienopyrimidinone portion of the compounds of formula (1) and (2) are provided, for example, in published PCT application WO 03/050064. Scheme A in that application provides a route by which the thienopyrimidinone portions of compounds of formula (2a) can be prepared, and Schemes B-G provide routes by which the thienopyrimidinone portions of compounds of formula (2b) can be prepared. Compounds of formula (2c) can similarly be prepared from the available starting material corresponding to the appropriate thiophene isomer of compound B1. Methods to convert the protected amines attached to position 2 of the pyrimidinone ring of these thienopyrimidinone intermediates are known in the art, and can be found, for example, in U.S. Pat. Nos. 6,518,277; 6,667,300; 6,949,535; and 6,800,620, and in published U.S. Patent Application US 2006/0106038 and PCT application WO 2005/113554. Additional methods for synthesis of the compounds of formula (3) are disclosed in unpublished U.S. Patent Application Ser. No. 60/858,850, filed Nov. 13, 2006. These references also provide methods for determining the activity of these compounds as inhibitors of PI3Kδ; thus those methods are known in the art.

Certain of these compounds are highly active, and also highly selective for inhibition of PI3Kδ relative to their activity on other PI3K isoforms, as illustrated in the following table, where two compounds of formula (3) are compared to other PI3K inhibitors (reference compounds 4a and 4b) having similar purine and linking components:

TABLE 1

Activity and Selectivity of Selected PI3K Inhibitors

| Ref. No. | COMPOUND | Ki (nM) (PI3Kδ) | Selectivity (α/δ) | Selectivity (β/δ) | Selectivity (γ/δ) |
|---|---|---|---|---|---|
| 3d | | 40 | 1447 | 126 | 187 |

TABLE 1-continued

Activity and Selectivity of Selected PI3K Inhibitors

| Ref. No. | COMPOUND | Ki (nM) (PI3Kδ) | Selectivity (α/δ) | Selectivity (β/δ) | Selectivity (γ/δ) |
|---|---|---|---|---|---|
| 4a | [structure] | 7 | 2963 | 119 | 61 |
| 3e | [structure] | 6 | 528 | 123 | 28 |
| 4b | [structure] | 5 | 132 | 29 | 12 |

Compounds of the invention can be depicted in different tautomeric forms, and can include multiple isomers in some cases. The invention includes each tautomeric form that is generally considered stable by those skilled in the art. In particular, the purine rings of compounds of the invention can exist in different tautomeric forms, and each is included even though at times only one is depicted for convenience. It includes each individual isomer of each compound, except where a particular isomer is depicted in a way that excludes other isomers. For example, where compound (2d) is shown as a single isomer, it is intended to describe a material consisting primarily of that isomer and containing only minor amounts of the opposite enantiomer, such as less than 20% or less than 10%; preferably, a specifically depicted isomer contains less than 5% of the enantiomeric isomer.

Some of the compounds of the invention can exist as separable rotational isomers, or atropisomers, and the invention includes use of each of these isomers. However, in some instances one of the atropisomers is preferred, or a single atropisomer is preferred over a mixture of such isomers. For example, where compound (2c') is shown as a single isomer, it is intended to describe a material consisting primarily of that isomer and containing only minor amounts of the opposite atropisomer, such as less than 20% or less than 10%; preferably, a specifically depicted atropisomer contains less than 5% of the enantiomeric atropisomer. Atropisomers in this type of compound have been found to exhibit surprising differences in pharmacokinetic behavior, resulting in substantially different biological activities such as differential absorption rates, and different metabolic rates. Thus even when two atropisomers provide similar direct effects on the pathway in cellular assays, they can provide quite different PK profiles as demonstrated by different AUC and $t_{1/2}$ values.

The invention further includes mixtures of isomers, including racemic mixtures and mixtures enriched in any particular isomer. In some embodiments, one isomer is preferred as indicated herein; however, as is well known, the other isomer may be present in addition to the preferred isomer without departing from the scope of the invention. Where the linking group between the quinazolinone ring and a purine heterocycle contains a chiral carbon, the S isomer of that chiral center is sometimes preferred.

The compounds of the invention can often be obtained and used as salts. In some embodiments, salts of the compounds of the invention are used in methods of treating liver disorders; in such embodiments, the salts are often pharmaceutically acceptable salts. 'Pharmaceutically acceptable' salts are well known in the art, and include acid addition salts and base addition salts that comprise a counterion that is not significantly detrimental when administered along with a compound of the invention to a subject in need of treatment.

"Pharmaceutically acceptable salts" refer to any salt that is physiologically acceptable insofar as it is compatible with other ingredients of the formulation and not deleterious to the recipient thereof. Some specific preferred examples are: acetate, trifluoroacetate, hydrochloride, methanesulfonate, succinate, malonate, maleate, hydrobromide, sulfate, citrate, tartrate, glycolate, and oxalate salts, which may be formed when the compound includes a basic (protonatable) feature. Similarly, the pharmaceutically acceptable salts include base addition products when the compound of the invention includes an acidic (de-protonatable) feature. Non-limiting examples of counterions for the deprotonated compounds of the invention include sodium, magnesium, calcium, ammonium, potassium, lithium, zinc, and similar cations.

As previously described, the term "PI3Kδ selective inhibitor" or "PI3Kβ selective inhibitor" generally refers to a compound that inhibits the activity of the PI3Kδ or β isozyme more effectively than other isozymes of the PI3K family. The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a PI3Kδ selective inhibitor alternatively can be understood to refer to a compound that exhibits a 50% inhibitory concentration ($IC_{50}$) with respect to PI3Kδ that is at least 10-fold, in another aspect at least 20-fold, and in another aspect at least 30-fold, lower than the $IC_{50}$ value with respect to any or all of the other Class I PI3K family members. In an alternative embodiment of the invention, the term PI3Kδ selective inhibitor can be understood to refer to a compound that exhibits an $IC_{50}$ with respect to PI3Kδ that is at least 50-fold, in another aspect at least 100-fold, in an additional aspect at least 200-fold, and in yet another aspect at least 500-fold, lower than the $IC_{50}$ with respect to any or all of the other PI3K Class I family members. A PI3Kδ selective inhibitor is typically administered in an amount such that it selectively inhibits PI3Kδ activity in vivo, as described above.

PI3Kβ selective inhibitors are similarly defined, where the above descriptions relate to PI3Kβ instead of PI3Kδ.

PI3Kγ selective inhibitors are similarly defined, where the above descriptions relate to PI3Kγ instead of PI3Kδ.

In some embodiments, the methods of the invention employ more than one compound of the invention to achieve a target level of selectivity among the isoforms of PI3K. Thus the invention includes methods using two compounds selected from the compounds disclosed herein to treat a liver disorder. The two compounds are typically selective for different isoforms of PI3K, and may be administered together, as individual compositions or combined in a single composition; or they may be administered separately, including administration on different schedules and/or by different routes of administration.

In some embodiments, the compound is selected from the compounds in Table 1 above.

In some embodiments, the methods utilize a compound selected from the following group:

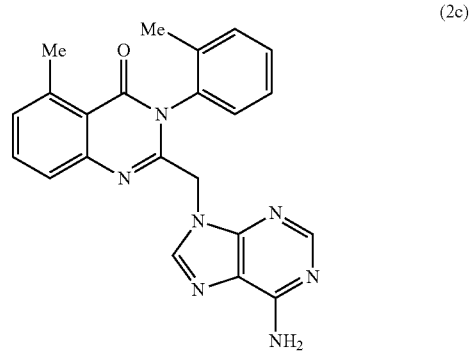 [SMILES: Cc1ccccc1-n1c(Cn2cnc3c(N)ncnc32)nc2cccc(C)c2c1=O]

(2c)

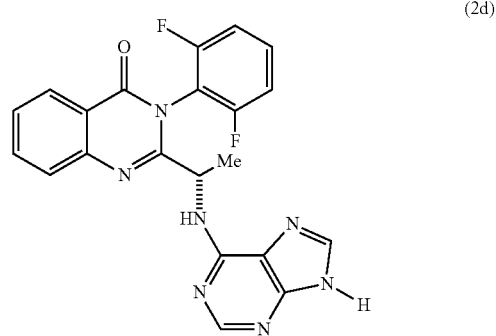

(2d)

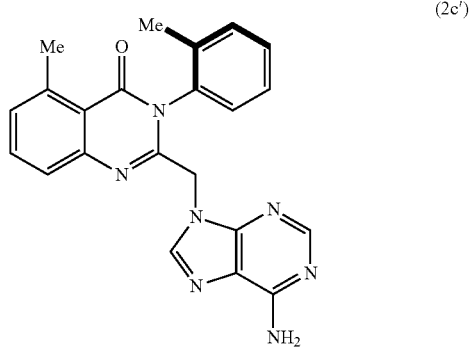

(2c')

(2c″)

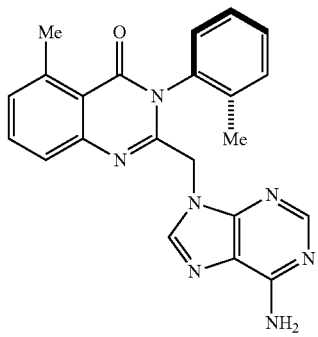

(4a)

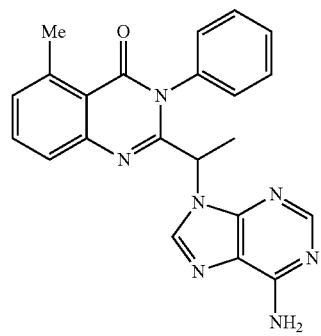

(4b)

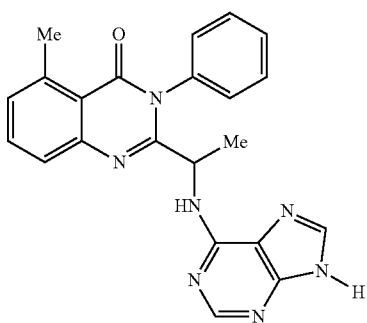

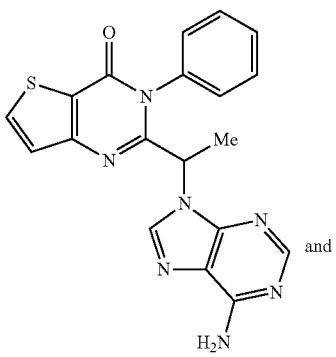

and

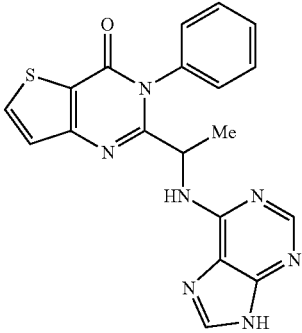 [SMILES: CC(Nc1ncnc2[nH]cnc12)c1nc2ccsc2c(=O)n1-c1ccccc1]

The subject for the treatments disclosed herein is a mammal, such as a human, afflicted with a liver disorder such as nonalcoholic fatty liver disease (NAFLD), non-alcoholic steatohepatitis (NASH), cirrhosis, hepatitis, liver adenoma, insulin hypersensitivity, or a liver cancer such as hepatocellular carcinoma. In some embodiments, the subject is one diagnosed with NAFLD or NASH, or a subject diagnosed with cirrhosis not associated with alcohol consumption. Alternatively, the subject may be at risk of NAFLD or NASH, and the methods of the invention may be used to prevent or delay development of NAFLD or NASH.

In some embodiments, the subject's Pten level is determined, and the subject is identified as a suitable subject for treatment by the present methods if the subject's Pten level is lower than normal for the subject's population, considering age and gender. In one embodiment, the subject is suitable for treatment by the present methods if the subject's Pten level is about half, or less than half, of the level that would be normal for the subject based on the subject's gender and age.

In some embodiments, a subject's lipid levels are determined in order to determine whether the subject is an especially good candidate for treatment with the compounds of the invention. In one embodiment, the subject's liver triglyceride level (in mg/g) is compared to the subject's serum triglyceride level (in mg/dl), and the subject is considered particularly suitable for treatment with a PI3K inhibitor if the subject's liver triglyceride level is higher than the subject's serum triglyceride level.

The compounds of the invention are readily prepared from available starting material using methods that are known in the art. Examples of methods for synthesizing the compounds useful in the methods of the invention are provided in U.S. Pat. Nos. 6,518,277; 6,667,300; 6,949,535; and 6,800,620, and in published U.S. Patent Application US 2006/0106038 and PCT application WO 2005/113554. These references also provide methods for determining the activity of these compounds as selective inhibitors of PI3Kδ or PI3Kβ, etc. Thus methods for making and selecting a selective inhibitor for use in the methods described herein are known.

The inhibitors of the invention may be covalently or non-covalently associated with a carrier molecule including but not limited to a linear polymer (e.g., polyethylene glycol, polylysine, dextran, etc.), a branched-chain polymer (see U.S. Pat. Nos. 4,289,872 and 5,229,490; PCT Publication No. WO 93/21259), a lipid, a cholesterol group (such as a steroid), or a carbohydrate or oligosaccharide. Specific examples of carriers for use in the pharmaceutical compositions of the invention include carbohydrate-based polymers such as trehalose, mannitol, xylitol, sucrose, lactose, sorbitol, dextrans such as cyclodextran, cellulose, and cellulose derivatives.

Also, the use of liposomes, microcapsules or microspheres, inclusion complexes, or other types of carriers is contemplated.

Other carriers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Still other useful carrier polymers known in the art include monomethoxy-polyethylene glycol, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers.

Methods include administration of an inhibitor to an individual in need, by itself, or in combination as described herein, and in each case optionally including one or more suitable diluents, fillers, salts, disintegrants, binders, lubricants, glidants, wetting agents, controlled release matrices, colorants/flavoring, carriers, excipients, buffers, stabilizers, solubilizers, other materials well known in the art and combinations thereof.

Any pharmaceutically acceptable (i.e., sterile and nontoxic) liquid, semisolid, or solid diluents that serve as pharmaceutical vehicles, excipients, or media may be used. Exemplary diluents include, but are not limited to, polyoxyethylene sorbitan monolaurate, magnesium stearate, calcium phosphate, mineral oil, cocoa butter, and oil of theobroma, methyl- and propylhydroxybenzoate, talc, alginates, carbohydrates, especially mannitol, α-lactose, anhydrous lactose, cellulose, sucrose, dextrose, sorbitol, modified dextrans, gum acacia, and starch. Some commercially available diluents are Fast-Flo®, Emdex®, STA-Rx 1500®, Emcompress® and Avicel®. Such compositions may influence the physical state, stability, rate of in vivo release, and rate of in vivo clearance of the PI3Kδ inhibitor compounds (see, e.g., *Remington's Pharmaceutical Sciences*, 18th Ed. pp. 1435-1712 (1990), which is incorporated herein by reference).

Pharmaceutically acceptable fillers can include, for example, lactose, microcrystalline cellulose, dicalcium phosphate, tricalcium phosphate, calcium sulfate, dextrose, mannitol, and/or sucrose.

Inorganic salts including calcium triphosphate, magnesium carbonate, and sodium chloride may also be used as fillers in the pharmaceutical compositions Amino acids may be used such as use in a buffer formulation of the pharmaceutical compositions.

Disintegrants may be included in solid dosage formulations of the inhibitors. Materials used as disintegrants include but are not limited to starch including the commercial disintegrant based on starch, Explotab®. Sodium starch glycolate, Amberlite®, sodium carboxymethylcellulose, ultramylopectin, sodium alginate, gelatin, orange peel, acid carboxymethylcellulose, natural sponge and bentonite may all be used as disintegrants in the pharmaceutical compositions. Other disintegrants include insoluble cationic exchange resins. Powdered gums including powdered gums such as agar, karaya or tragacanth may be used as disintegrants and as binders. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to facilitate granulation of the therapeutic ingredient.

An antifrictional agent may be included in the formulation of the therapeutic ingredient to prevent sticking during the formulation process. Lubricants may be used as a layer between the therapeutic ingredient and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax® 4000 and 6000.

Glidants that might improve the flow properties of the therapeutic ingredient during formulation and to aid rearrangement during compression might be added. Suitable glidants include starch, talc, pyrogenic silica and hydrated silicoaluminate.

To aid dissolution of the therapeutic into the aqueous environment, a surfactant might be added as a wetting agent. Natural or synthetic surfactants may be used. Surfactants may include anionic detergents such as sodium lauryl sulfate, dioctyl sodium sulfosuccinate, and dioctyl sodium sulfonate. Cationic detergents such as benzalkonium chloride and benzethonium chloride may be used. Nonionic detergents that can be used in the pharmaceutical formulations include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants can be present in the pharmaceutical compositions of the invention either alone or as a mixture in different ratios.

Controlled release formulation may be desirable. The inhibitors of the invention can be incorporated into an inert matrix which permits release by either diffusion or leaching mechanisms, e.g., gums. Slowly degenerating matrices may also be incorporated into the pharmaceutical formulations, e.g., alginates, polysaccharides. Another form of controlled release is a method based on the Oros® therapeutic system (Alza Corp.), i.e., the drug is enclosed in a semipermeable membrane which allows water to enter and push the inhibitor compound out through a single small opening due to osmotic effects. Some enteric coatings also have a delayed release effect.

Colorants and flavoring agents may also be included in the pharmaceutical compositions. For example, the inhibitors of the invention may be formulated (such as by liposome or microsphere encapsulation) and then further contained within an edible product, such as a beverage containing colorants and flavoring agents.

The therapeutic agent can also be given in a film coated tablet. Non-enteric materials for use in coating the pharmaceutical compositions include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, povidone and polyethylene glycols. Enteric materials for use in coating the pharmaceutical compositions include esters of phthalic acid. A mix of materials might be used to provide the optimum film coating. Film coating manufacturing may be carried out in a pan coater, in a fluidized bed, or by compression coating.

The compositions can be administered in solid, semi-solid, liquid or gaseous form, or may be in dried powder, such as lyophilized form. The pharmaceutical compositions can be packaged in forms convenient for delivery, including, for example, capsules, sachets, cachets, gelatins, papers, tablets, capsules, suppositories, pellets, pills, troches, lozenges or other forms known in the art. The type of packaging will generally depend on the desired route of administration.

Implantable sustained release formulations are also contemplated, as are transdermal formulations.

In the methods according to the invention, the inhibitor compounds may be administered by various routes. For example, pharmaceutical compositions may be for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release, e.g., embedded under the splenic capsule, brain, or in the cornea); by sublingual, anal, vaginal, or by surgical implantation, e.g., embedded under the splenic capsule, brain, or in the cornea. The treatment may consist of a single dose or a plurality of doses over a period of time. In general, the methods of the invention involve administering effective amounts of an inhibitor of the invention together with pharmaceutically acceptable diluents, preservatives, solubilizers, emulsifiers, adjuvants and/or carriers, as described above.

In one aspect, the invention provides methods for oral administration of a pharmaceutical composition of the invention. Oral solid dosage forms are described generally in *Remington's Pharmaceutical Sciences*, supra at chapter 89. Solid dosage forms include tablets, capsules, pills, troches or lozenges, and cachets or pellets. Also, liposomal or proteinoid encapsulation may be used to formulate the compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation will include a compound of the invention and inert ingredients which protect against degradation in the stomach and which permit release of the biologically active material in the intestine.

The inhibitors can be included in the formulation as fine multiparticulates in the form of granules or pellets of particle size about 1 mm The formulation of the material for capsule administration could also be as a powder, lightly compressed plugs or even as tablets. The capsules could be prepared by compression.

Also contemplated herein is pulmonary delivery of the PI3K inhibitors in accordance with the invention. According to this aspect of the invention, the inhibitor is delivered to the lungs of a mammal by inhalation of a suitable composition, and the PI3K inhibitor traverses across the lung epithelial lining to the blood stream.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the UltraVent™ nebulizer, manufactured by Mallinckrodt, Inc., St. Louis, Mo.; the Acorn II® nebulizer, manufactured by Marquest Medical Products, Englewood, Colorado; the Ventolin® metered dose inhaler, manufactured by Glaxo Inc., Research Triangle Park, North Carolina; and the Spinhaler® powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

In practice of the methods of the invention, the pharmaceutical compositions are generally provided in doses ranging from 1 pg compound/kg body weight to 1000 mg/kg, 0.01 mg/kg to 100 mg/kg, 0.1 mg/kg to 20 mg/kg, given in daily doses or in equivalent doses at longer or shorter intervals, e.g., every other day, twice weekly, weekly, or twice or three times daily. The inhibitor compositions may be administered by an initial bolus followed by a continuous infusion to maintain therapeutic circulating levels of drug product. Those of ordinary skill in the art will readily optimize effective dosages and administration regimens as determined by good medical practice and the clinical condition of the individual to be treated. The frequency of dosing will depend on the pharmacokinetic parameters of the agents and the route of administration.

The optimal pharmaceutical formulation will be determined by one skilled in the art depending upon the route of administration and desired dosage (see, for example, *Remington's Pharmaceutical Sciences*, latest ed., the disclosure of which is hereby incorporated by reference). Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in human clinical trials. Appropriate dosages may be ascertained by using established assays for determining blood level dosages in conjunction with an appropriate physician considering various factors which modify the action of drugs, e.g., the drug's specific activity, the severity of the indication, and the responsiveness of the individual, the age, condition, body weight, sex and diet of the individual, the time of administration and other clinical factors. As studies are conducted, further information will emerge regarding the appropriate dosage levels and duration of treatment for various indications involving aberrant proliferation of hematopoietic cells.

The following enumerated items are additional embodiments of the invention:

1. In one embodiment, the invention provides a method to treat a liver disorder, which method comprises administering to a subject in need thereof an effective amount of a selective inhibitor of at least one isoform of PI3K kinase.

2. The method of embodiment 1, wherein the inhibitor is selective for inhibition of PI3Kδ or PI3Kβ or both, relative to its inhibition of other Class I PI3K isoforms.

3. The method of embodiment 1 or 2, wherein the disorder is nonalcoholic steatohepatatis.

4. The method of embodiment 1 or 2, wherein the liver disorder is nonalcoholic fatty liver disease (NAFLD), hepatic steatosis, cirrhosis, hepatitis, a liver adenoma, insulin hypersensitivity, or a liver cancer.

5. The method of any of embodiments 1-4, wherein the inhibitor is a compound of formula (1a) or formula (1b):

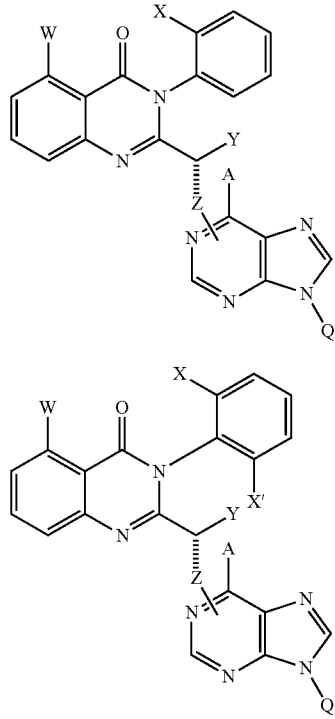

wherein:
W is selected from the group consisting of H, Me, Cl, and F;
X and X' are independently selected from the group consisting of H, Me, Cl, and F;
Y is selected from the group consisting of H, Me and Et;
Z is NH or a bond; and A is NH$_2$, or A is absent and indicates the point of attachment of Z to the purine ring;
Q is H when A is absent, or Q is absent and indicates the point of attachment of Z to the purine ring when A is NH$_2$;
provided that not more than two of W, X, and Y represents H;
or a pharmaceutically acceptable salt thereof.
6. The method of embodiment 5, wherein not more than one of W, X, and Y represents H.
7. The method of any of embodiments 5-6, wherein W is Me.
8. The method of any of embodiments 5-7, wherein X is H, Me or F.
9. The method of any of embodiments 5-8, wherein Z is NH.
10. The method of any of embodiments 5-8, wherein Z is a bond.
11. The method of embodiment 9 or 10, wherein A is absent and Q is H.
12. The method of embodiment 9 or 10, wherein A is NH$_2$ and Q indicates the point of attachment of Z to the purine ring.
13. The method of any of embodiments 5-12, wherein at least one of W, X and Y is Me.
14. The method of any of embodiments 5-13, wherein Y is H.
15. The method of any of embodiments 5-13, wherein Y is Me.
16. The method of any of embodiments 5-13, wherein Y is Et.
17. The method of any one of embodiments 5-16, wherein the compound is a compound of formula (1b), and wherein X and X' are different.
18. The method of embodiment 17, wherein X' is H, and X is selected from Cl and Me.
19. The method of any one of embodiments 1-4, wherein the inhibitor is a compound of formula (3):

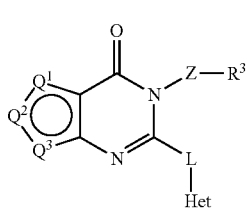

wherein:
one of $Q^1$, $Q^2$ and $Q^3$ is S, and the other of two of $Q^1$, $Q^2$ and $Q^3$ are —$CR^1$—;
wherein each $R^1$ is independently H, halo, OR, NR$_2$, NROR, NRNR$_2$, SR, SOR, SO$_2$R, SO$_2$NR$_2$, NRSO$_2$R, NRCONR$_2$, NRCOOR, NRCOR, CF$_3$, CN, COOR, CONR$_2$, OOCR, COR, or NO$_2$,
or $R^1$ can be an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, and C6-C12 heteroarylalkyl groups,
wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
and wherein two R on the same atom or on adjacent atoms can be linked to form a 3-8 membered ring, optionally containing one or two N, O or S as ring members;
and wherein each R group other than H, and each ring formed by linking two R groups together, is optionally substituted;
Z is a bond, or is O, NR$^2$, C1-C6 alkylene or C1-C6 heteroalkylene, each of which is optionally substituted with up to two C1-C6 alkyl or C2-C6 heteroalkyl groups, where two of said alkyl or heteroalkyl groups can optionally cyclize to form a 3-7 membered ring containing up to two heteroatoms selected from O, N and S as ring members;
$R^3$ is aryl, heteroaryl, cycloalkyl, or heterocycloalkyl, each of which is optionally substituted with up to three $R^1$, or $R^3$ can be H if Z is not a bond;
L is selected from the group consisting of —C(R$^2$)$_2$—, —C(R$^2$)$_2$—C(R$^2$)$_2$—, —C(R$^2$)$_2$—NR$^2$—, and —C(R$^2$)$_2$—S(O)$_n$—,
wherein each $R^2$ is independently H or an optionally substituted member selected from C1-C6 alkyl, C2-C6 heteroalkyl, C2-C6 alkenyl, and C2-C6 alkynyl, and n is 0-2;

and two R² , if present on L, can cyclize to form a 3-7 membered ring that may contain up to two heteroatoms selected from N, O and S as ring members;

Het is a monocyclic or bicyclic ring system wherein at least two ring atoms are N and wherein at least one ring is aromatic, and Het is optionally substituted with up to three substituents selected from R⁴, N(R⁴)₂, S(O)ₚR⁴, OR⁴, halo, CF₃, CN, NR⁴OR⁴, NR⁴N(R⁴)₂, SR⁴, SOR⁴, SO₂R⁴, SO₂N(R⁴)₂, NR⁴SO₂R⁴, NR⁴CON(R⁴)₂, NR⁴COOR⁴, NR⁴COR⁴, CN, COOR⁴, CON(R⁴)₂, OOCR⁴, COR⁴, or NO₂, wherein each R⁴ is independently H or an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, and C6-C12 heteroarylalkyl, and wherein two R⁴ on the same atom or on adjacent atoms can be linked to form a 3-8 membered ring, optionally containing one or two heteroatoms selected from N, O and S;

wherein the optional substituents on each optionally substituted alkyl, heteroalkyl, alkenyl, heteroalkenyl, alkynyl, heteroalkynyl, acyl, heteroacyl, aryl, heteroaryl, arylalkyl and heteroarylalkyl are selected from C1-C4 alkyl, halo, CF₃, CN, =O, =N—CN, =N—OR', =NR', OR', NR'₂, SR', SO₂R', SO₂NR'₂, NR'SO₂R', NR'CONR'₂, NR'COOR', NR'COR', CN, COOR', CONR'₂, OOCR', COR', and NO₂, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' on the same or adjacent atoms can be linked to form a 3-7 membered ring optionally containing up to three heteroatoms selected from N, O and S; and p is 0-2;

or a pharmaceutically acceptable salt thereof.

20. The method of embodiment 19, wherein the inhibitor is a compound of formula (3a), (3b), or (3c):

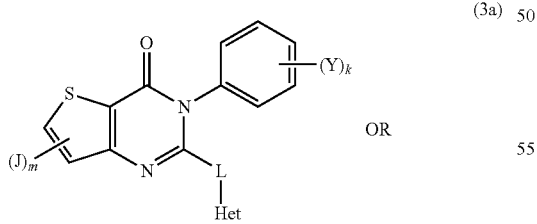

(3a)

OR

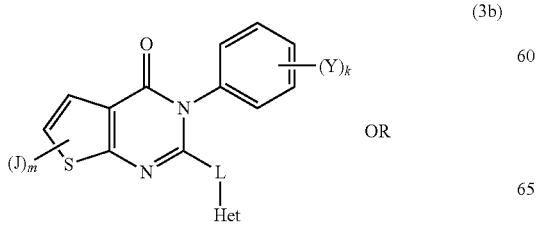

(3b)

OR

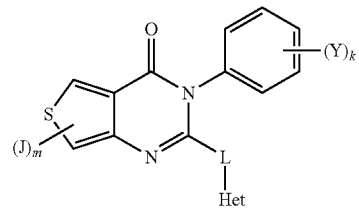

(3c)

wherein:

each J and each Y is independently selected from the group consisting of F, Cl, Br, CN, Me, CF₃, OMe, CONR²₂, COOR², NMe₂, NH₂, NHMe, -Q-(CH₂)_q—OR², and -Q-(CH₂)_q-N(R²)₂, where q is 0-4, and Q is absent or is selected from O, S and NR²;

m is 0-2, and k is 0-3;

L is selected from —C(R²)₂—, —C(R²)₂—NR²—, and —C(R²)₂—S—, each R² is independently H or an optionally substituted C1-C4 alkyl, C2-C4 alkenyl, or C2-C4 alkynyl, or an optionally substituted C2-C4 heteroalkyl;

and two R², if present on a single atom or on adjacent atoms, can cyclize to form a 3-7 membered ring that is optionally substituted and may contain up to two heteroatoms selected from N, O and S as ring members;

Het is selected from the group consisting of:

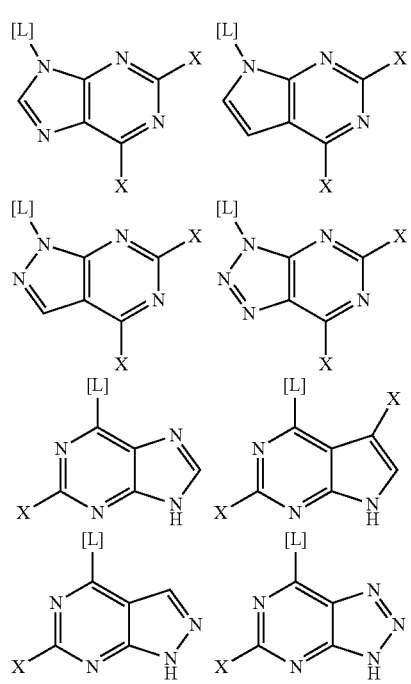

wherein [L] indicates the atom of Het to which L is attached; and each X is independently H, F, Cl, Br, Me, CF₃, OH, OMe, NH₂, NHAc, or NHMe;

and the optional substituents on each optionally substituted alkyl, heteroalkyl, alkenyl, heteroalkenyl, alkynyl, heteroalkynyl, acyl, heteroacyl, aryl, heteroaryl, arylalkyl and heteroarylalkyl are selected from C1-C4 alkyl, halo, =O, =N—CN, =N—OR', =NR', OR', NR'₂, SR', SO₂R', SO₂NR'₂, NR'SO₂R', NR'CONR'₂, NR'COOR', NR'COR', CN, COOR', CONR'₂, OOCR', COR', and NO₂, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' on the same or adjacent atoms can be linked to form a 3-7 membered ring optionally containing up to three heteroatoms selected from N, O and S;

and p is 0-2;

or a pharmaceutically acceptable salt thereof.

21. The method of embodiment 4, wherein the compound is selected from the group consisting of:

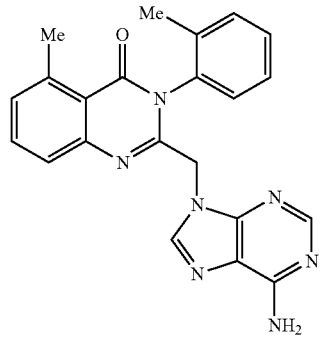
(2c)

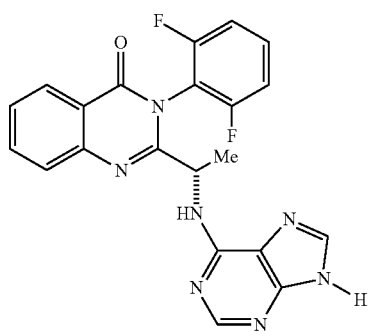
(2d)

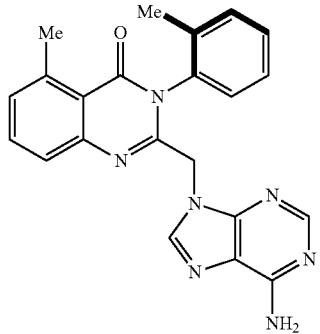
(2c')

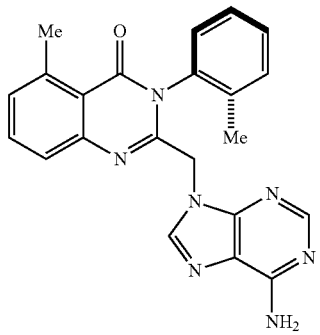
(2c")

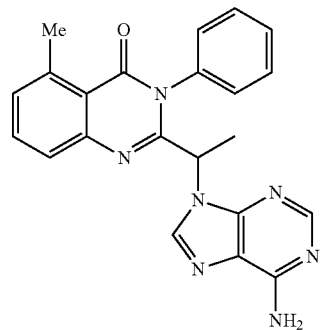
(4a)

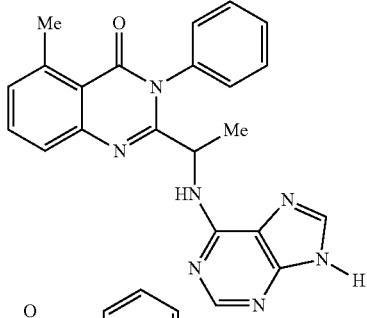
(4b)

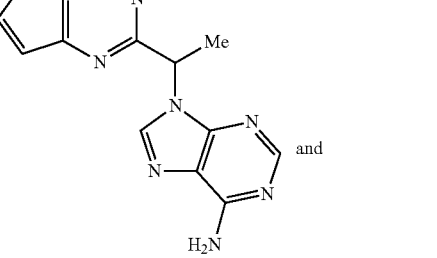
and

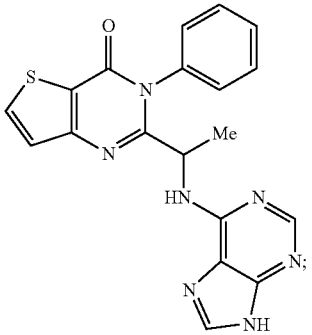

and the pharmaceutically acceptable salts thereof.

22. The method of any of the preceding embodiments, wherein the subject is one having a reduced levels of hepatic Pten activity.

23. The method of embodiment 22, wherein the subject has a Pten mutation.

The following examples are offered to illustrate but not to limit the invention.

EXAMPLE 1

Preparation of 2-((6-amino-9H-purin-9-yl)methyl)-5-methyl-3-o-tolylquinazolin-4(3H)-one 2-amino-6-methylbenzoic acid is reacted with 2-chloroacetyl chloride to produce the 2-(-2-chloroacetamido)-6-methylbenzoic acid. Reaction with o-toluidine and phosphoryl trichloride yields the cyclized intermediate. Further reaction with diBOC-protected adenine give the BOC protected product, which is deprotected resulting in 2-((6-amino-9H-purin-9-yl) methyl)-5-methyl-3-o-tolylquinazolin-4(3H)-one (2c).

The atropisomers of compound (2c) may be resolved by high-pressure liquid chromatography (HPLC).

EXAMPLE 2

Preparatory HPLC Separation of Atropisomers

This example demonstrates the separation of the two atropisomers of compound (2c) using HPLC.

A small sample of the enantiomeric mixture was dissolved in isopropanol at a concentration of 1.45 mg/mL and 5 µL injected into a normal phase column using the following conditions: CHIRALPAK® IA, 4.6 mm ID×250 mm L, 40/60/0.1 hexanes/IPA/DEA, 0.8 mL/min, 30° C. Two peaks are resolved at 8.7 min. and 13.0 min These analytical conditions and HPLC trace were used to identify the compositions of the separated products.

2.80 g of compound (2c) was separated on a CHIRALPAK® IA preparative column using 40/60/0.1 hexanes/IPA/DEA mobile phase at room temperature and using a detection wavelength of 275 nm. Two enantiomers were isolated, (2c') and (2c"), and were cleanly separated from each other. It was not immediately determined which peak corresponded to which atropisomer.

1.24 g of the first eluted enantiomer, atropisomer was isolated, and was analyzed under the analytical method described above (0.96 mg in 0.8 mL IPA). The HPLC trace has a major peak at 8.7 min and indicates 99.0% e.e.

1.38 g of the second eluted enantiomer, atropisomer was isolated, and was analyzed under the same analytical method (1.72 mg in 1 mL IPA) described above. The HPLC trace has a major peak at 13.0 min and indicates 98.8% e.e.

For purposes of discussion, resolved atropisomers of compound (2c) that were isolated by normal phase chromatographic separation and eluted at time 8.7 min and 13.0 min as described in this example, will be referred to as atropisomers (2c') and (2c").

EXAMPLE 3

Treatment of NASH in Pten Knock-out Mice

Sato, et al. describe production of Pten KO mice that are a suitable model for certain NASH patient populations, and exhibit all stages of NASH (inflammation; fibrosis' and carcinogenesis), beginning by about 10 weeks of age. Compounds of the invention can therefore be shown to be effective for treating NASH by their efficacy in delaying progression of symptomology in such Pten KO mice.

Pten KO mice as described by Sato, et al. (*Hepatology Res.*, vol 34, 256-65 (2006)) are produced as described, and are treated with a compound described herein beginning at 6 weeks of age. The compound can be administered orally or by injection, at an initial dosage of 100 mg/kg/day. Progression of NASH is measured as described in Sato, and is compared to progression in untreated (control) Pten KO mice. Dosage can be adjusted up or down in the treated mice at 10 weeks of age, depending upon the effectiveness of the initial dosage. The mice are assessed weekly until 35 weeks of age; dosage is adjusted as needed based on biopsy analyses of the livers of treated mice in comparison to controls. Statistically significant reduction of the progression of NASH in these mice demonstrates usefulness for treating NASH.

EXAMPLE 4

Cell Culture Testing of Compounds

Sato et al. (Id.) also describes isolation of hepatocytes from Pten KO mice. The compounds of the invention can be tested in cultured hepatocytes to demonstrate their effectiveness for slowing progression of cellular abnormalities associated with NASH.

EXAMPLE 5

In Vivo Model for NASH Treatment

Horie, et al. (*J. Clinical Investigation*, vol. 112(12), 1774-1783 (2004)) describes generation of AlbCrePtet$^{flox/flox}$ mice, which were shown to be highly prone to hepatomegaly and steatohepatitis. These mice can be used to demonstrate the effectiveness of compounds of the invention for treating these NASH-like conditions.

The AlbCrePten$^{flox/flox}$ mice as described by Horie, et al., are treated with a compound described herein beginning at 6 weeks of age. The compound can be administered orally or by injection, at an initial dosage of 100 mg/kg/day. Progression of NASH-like symptoms is measured, and is compared to progression in untreated (control) mice. Dosage can be adjusted up or down in the treated mice at 10 weeks of age, depending upon the effectiveness of the initial dosage. The mice are assessed weekly until 35 weeks of age; dosage is adjusted as needed based on biopsy analyses of the livers of treated mice in comparison to controls. Statistically significant reduction of the progression of hepatomegaly and/or steatohepatitis in these mice demonstrates usefulness for treating NASH.

The invention claimed is:

1. A method to treat a liver disorder, which method comprises administering to a subject in need thereof an effective amount of a selective inhibitor of at least one isoform of PI3K kinase.

2. The method of claim 1, wherein the inhibitor is selective for inhibition of PI3Kδ or PI3Kβ or both, relative to its inhibition of other Class I PI3K isoforms.

3. The method of claim 2, wherein the disorder is nonalcoholic steatohepatitis.

4. The method of claim 2, wherein the liver disorder is nonalcoholic fatty liver disease (NAFLD), hepatic steatosis, cirrhosis, hepatitis, a liver adenoma, insulin hypersensitivity, or a liver cancer.

5. The method of claim 1, wherein the inhibitor is a compound of formula (1a) or formula (1b):

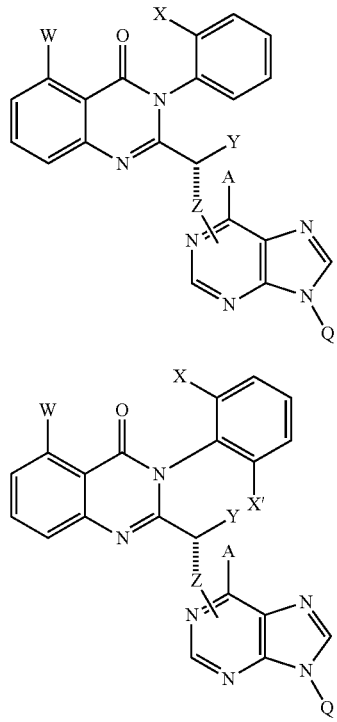

wherein:
W is selected from the group consisting of H, Me, Cl, and F;
X and X' are independently selected from the group consisting of H, Me, Cl, and F;
Y is selected from the group consisting of H, Me and Et;
Z is NH or a bond; and
A is $NH_2$, or A is absent and indicates the point of attachment of Z to the purine ring;
Q is H when A is absent, or Q is absent and indicates the point of attachment of Z to the purine ring when A is $NH_2$;
provided that not more than two of W, X, and Y represents H;
or a pharmaceutically acceptable salt thereof.

6. The method of claim 5, wherein not more than one of W, X, and Y represents H.

7. The method of claim 5, wherein W is Me, and/or wherein X is H, Me or F.

8. The method of claim 5, wherein Z is NH.

9. The method of claim 5, wherein Z is a bond.

10. The method of claim 8, wherein A is absent and Q is H.

11. The method of claim 9, wherein A is $NH_2$ and Q indicates the point of attachment of Z to the purine ring.

12. The method of claim 10, wherein at least one of W, X and Y is Me.

13. The method of claim 11, wherein at least one of W, X and Y is Me.

14. The method of claim 10, wherein Y is Me or Et.

15. The method of claim 11, wherein Y is H.

16. The method of claim 5, wherein the compound is a compound of formula (1b), and wherein X and X' are different.

17. The method of claim 15, wherein X' is H, and X is selected from Cl and Me.

18. The method of claim 1, wherein the inhibitor is a compound of formula (3):

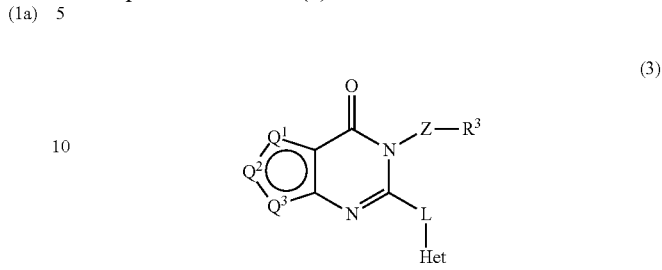

wherein:
one of $Q^1$, $Q^2$ and $Q^3$ is S, and the other of two of $Q^1$, $Q^2$ and $Q^3$ are $—CR^1—$;
wherein each $R^1$ is independently H, halo, OR, $NR_2$, NROR, $NRNR_2$, SR, SOR, $SO_2R$, $SO_2NR_2$, $NRSO_2R$, $NRCONR_2$, NRCOOR, NRCOR, $CF_3$, CN, COOR, $CONR_2$, OOCR, COR, or $NO_2$,
or $R^1$ can be an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, and C6-C12 heteroarylalkyl groups,
wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
and wherein two R on the same atom or on adjacent atoms can be linked to form a 3-8 membered ring, optionally containing one or two N, O or S as ring members;
and wherein each R group other than H, and each ring formed by linking two R groups together, is optionally substituted;
Z is a bond, or is O, $NR^2$, C1-C6 alkylene or C1-C6 heteroalkylene, each of which is optionally substituted with up to two C1-C6 alkyl or C2-C6 heteroalkyl groups, where two of said alkyl or heteroalkyl groups can optionally cyclize to form a 3-7 membered ring containing up to two heteroatoms selected from O, N and S as ring members;
$R^3$ is aryl, heteroaryl, cycloalkyl, or heterocycloalkyl, each of which is optionally substituted with up to three $R^1$, or $R^3$ can be H if Z is not a bond;
L is selected from the group consisting of $—C(R^2)_2—$, $—C(R^2)_2—C(R^2)_2—$, $—C(R^2)_2—NR^2—$, and $—C(R^2)_2—S(O)_n—$,
wherein each $R^2$ is independently H or an optionally substituted member selected from C1-C6 alkyl, C2-C6 heteroalkyl, C2-C6 alkenyl, and C2-C6 alkynyl, and n is 0-2;
and two $R^2$, if present on L, can cyclize to form a 3-7 membered ring that may contain up to two heteroatoms selected from N, O and S as ring members;
Het is a monocyclic or bicyclic ring system wherein at least two ring atoms are N and wherein at least one ring is aromatic, and Het is optionally substituted with up to three substituents selected from $R^4$, $N(R^4)_2$, $S(O)_pR^4$, $OR^4$, halo, $CF_3$, CN, $NR^4OR^4$, $NR^4N(R^4)_2$, $SR^4$, $SOR^4$, SO₂R⁴, SO₂N(R⁴)₂, NR⁴SO₂R⁴, NR⁴CON(R⁴)₂, NR⁴COOR⁴, NR⁴COR⁴, CN, COOR⁴, CON(R⁴)₂, OOCR⁴, COR⁴, or NO₂, wherein each R⁴ is independently H or an optionally substituted member selected from the group consisting of C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, and C6-C12 heteroarylalkyl, and wherein two R⁴ on the same atom or on adjacent atoms can be linked to form a 3-8 membered ring, optionally containing one or two heteroatoms selected from N, O and S;

wherein the optional substituents on each optionally substituted alkyl, heteroalkyl, alkenyl, heteroalkenyl, alkynyl, heteroalkynyl, acyl, heteroacyl, aryl, heteroaryl, arylalkyl and heteroarylalkyl are selected from C1-C4 alkyl, halo, CF₃, CN, =O, =N—CN, =N—OR', =NR', OR', NR'₂, SR', SO₂R', SO₂NR'₂, NR'SO₂R', NR'CONR'₂, NR'COOR', NR'COR', CN, COOR', CONR'₂, OOCR', COR', and NO₂, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' on the same or adjacent atoms can be linked to form a 3-7 membered ring optionally containing up to three heteroatoms selected from N, O and S; and p is 0-2;

or a pharmaceutically acceptable salt thereof.

19. The method of claim 18, wherein the inhibitor is a compound of formula (3a), (3b), or (3c):

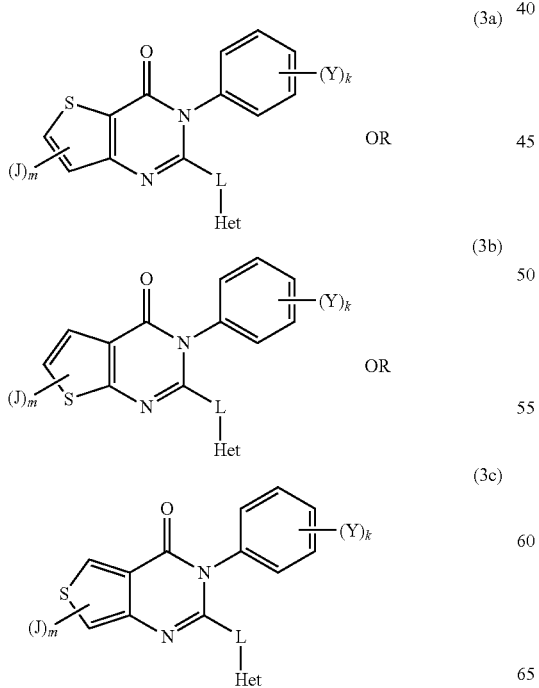

wherein:
each J and each Y is independently selected from the group consisting of F, Cl, Br, CN, Me, CF₃, OMe, CONR²₂, COOR², NMe₂, NH₂, NHMe, -Q-(CH₂)_q—OR², and -Q-(CH₂)_q—N(R²)₂, where q is 0-4, and Q is absent or is selected from O, S and NR²;

m is 0-2, and k is 0-3;

L is selected from —C(R²)₂—, —C(R²)₂—NR²—, and —C(R²)₂—S—, each R² is independently H or an optionally substituted C1-C4 alkyl, C2-C4 alkenyl, or C2-C4 alkynyl, or an optionally substituted C2-C4 heteroalkyl;

and two R², if present on a single atom or on adjacent atoms, can cyclize to form a 3-7 membered ring that is optionally substituted and may contain up to two heteroatoms selected from N, O and S as ring members;

Het is selected from the group consisting of:

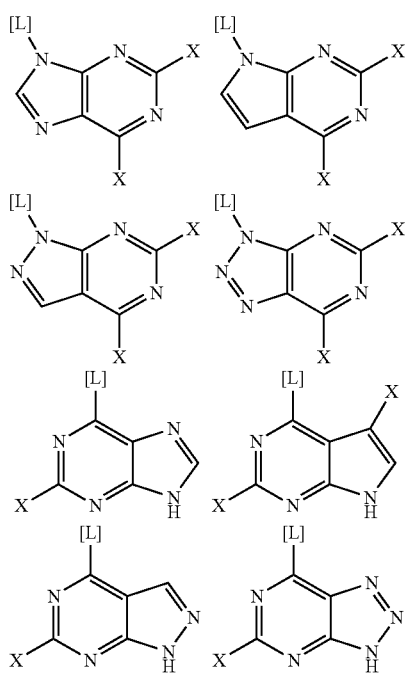

wherein [L] indicates the atom of Het to which L is attached; and each X is independently H, F, Cl, Br, Me, CF₃, OH, OMe, NH₂, NHAc, or NHMe;

and the optional substituents on each optionally substituted alkyl, heteroalkyl, alkenyl, heteroalkenyl, alkynyl, heteroalkynyl, acyl, heteroacyl, aryl, heteroaryl, arylalkyl and heteroarylalkyl are selected from C1-C4 alkyl, halo, =O, =N—CN, =N—OR', =NR', OR', NR'₂, SR', SO₂R', SO₂NR'₂, NR'SO₂R', NR'CONR'₂, NR'COOR', NR'COR', CN, COOR', CONR'₂, OOCR', COR', and NO₂, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' on the same or adjacent atoms can be linked to form a 3-7 membered ring optionally containing up to three heteroatoms selected from N, O and S;

and p is 0-2;

or a pharmaceutically acceptable salt thereof.

20. The method of claim 1, wherein the compound is selected from the group consisting of:
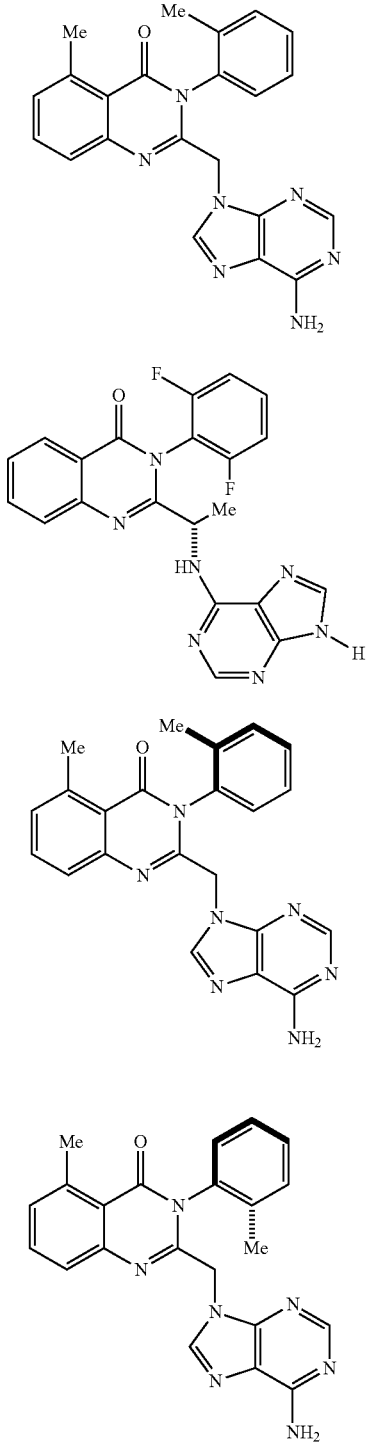
(2c)
(2d)
(2c′)
(2c″)
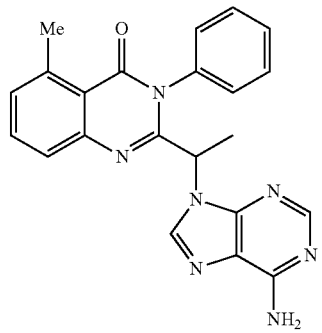
(4a)
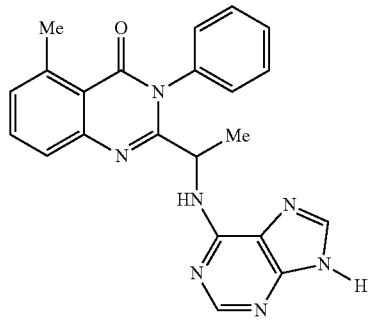
(4b)
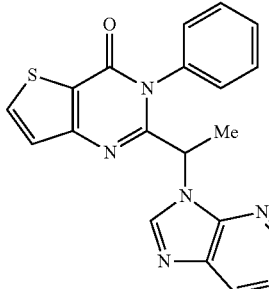
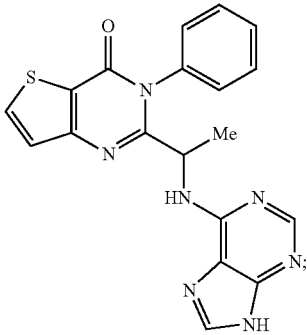
and
and the pharmaceutically acceptable salts thereof.
21. The method of claim 1, wherein the subject is one having a reduced levels of hepatic Pten activity.
22. The method of claim 21, wherein the subject has a Pten mutation.
* * * * *